(12) United States Patent
Giordano

(10) Patent No.: US 7,635,561 B2
(45) Date of Patent: Dec. 22, 2009

(54) METHODS OF DIAGNOSING, PROGNOSING AND TREATING BREAST CANCER

(75) Inventor: Antonio Giordano, Radnor, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 209 days.

(21) Appl. No.: 10/558,538

(22) PCT Filed: Jun. 1, 2004

(86) PCT No.: PCT/US2004/017308

§ 371 (c)(1),
(2), (4) Date: Feb. 27, 2006

(87) PCT Pub. No.: WO2005/027712

PCT Pub. Date: Mar. 31, 2005

(65) Prior Publication Data

US 2007/0092498 A1     Apr. 26, 2007

Related U.S. Application Data

(60) Provisional application No. 60/475,134, filed on May 30, 2003, provisional application No. 60/478,624, filed on Jun. 3, 2003.

(51) Int. Cl.
    *C12Q 1/68*           (2006.01)
    *G01N 33/53*       (2006.01)

(52) U.S. Cl. .............................. 435/6; 435/7.1; 435/7.8

(58) Field of Classification Search ...................... 435/6, 435/7.1, 7.8
See application file for complete search history.

(56) References Cited

U.S. PATENT DOCUMENTS

2003/0225015 A1    12/2003   Ward et al.

OTHER PUBLICATIONS

Iwase et al., British Journal of Cancer, 1999, vol. 80, No. 12, pp. 1982-1986.*
Macaluso et al., "pRb2/p130-E2F4/5-HDAC1-SUV39H1-P300 and pRb2/p130-E2F4/5-HDACI-SUV39H1-DNMT1 multimolecular complexes mediate the transcription of estrogen receptor-alpha in breast cancer", Oncogene, Jun. 2003, vol. 22, pp. 3511-3517.
Iwase et al, "DNA methylation analysis at distal and proximal promoter regions of the oestrogen receptor gene in breast cancers", British Journal of Cancer, 1999, vol. 80. No. 12, pp. 1982-1986.
Elbashir et al, Duplexes of 21-nucleotide RNAs mediate RNA interference in cultured mammalian cells. Nature, May 2001, vol. 411 pp. 494-498.
Lapidus, et al., "Mapping of ER gene CpG Island Methylation by Methylation-specific Polymerase Chain Reaction," Cancer Research 58, 2515-2519, Jun. 15, 1998.
Ferguson, et al., "Demethylation of the Estrogen Receptor Gene in Estrogen Receptor-negative Breast Cancer Cells Can Reactivate Estrogen Receptor Gene Expression," Cancer Research 55, 2279-2283, Jun. 1, 1995.
Yoshida, et al., Distinct Mechanisms of Loss of Estrogen Receptor α Gene Expression in Human Breast Cancer: Methylation of the Gene and Alteration of trans-acting Factors, Carcinogenesis, vol. 21, No. 12, 2193-2201, 2000.
Yan, et al., "Role of DNA Methylation and Histone Acetylation in Steroid Receptor Expression in Breast Cancer," Journal of Mammary Gland Biology and Neoplasia, vol. 6, No. 2, 183-192, 2001.
Cunningham, et al., Comparison of 5-Azacytidine (NSC-102816) With CCNU (NSC-79037) in the Treatment of Patients With Breast Cancer and Evaluation of the Subsequent Use of Cyclophosphamide (NSC-26271), Cancer Chemotherapy Reports, Part 1, vol. 58, No. 5, 677-681, Sep./Oct. 1974.

* cited by examiner

*Primary Examiner*—Janet L Epps-Smith
(74) *Attorney, Agent, or Firm*—Reed Smith LLP; William J. McNichol, Jr.

(57) ABSTRACT

The protein pRb2/p130 represses expression of the ER-α gene. Blocking pRb2/p130 expression or altering ER-α gene methylation to alter pRb2/p130 complex binding allows transcriptional activity of the ER-α gene to be restored. Detecting and regulating the methylation state of the ER-α gene, optionally together with detecting and regulating pRb2/p130 multimolecular complexes bound to the ER-α gene promoter, allows estrogen-insensitive breast cancer cells to be identified, so that an accurate prognosis can be obtained and an appropriate course of treatment administered. Also, inhibiting pRb2/p130, or altering the methylation pattern of the ER-α gene by targeting DNMT 1 In the pRb2/p 130-E2F4/5-HDAC 1-DNMT1-SUV39H1 complex, allows estrogen-insensitive breast cancer cells to be converted to estrogen-sensitive breast cancer cells. Estrogen-sensitive breast cancer cells which are generally more susceptible to current anti-cancer treatments.

4 Claims, 7 Drawing Sheets

SEQUENCE LISTING

<160> NUMBER OF SEQ ID NOS: 16

<210> SEQ ID NO 1
<211> LENGTH: 4853
<212> TYPE: DNA
<213> ORGANISM: Homo sapiens

<400> SEQUENCE: 1

| | | | | | |
|---|---|---|---|---|---|
| ttcgccgttt | gaattgctgc | gggcccgggc | cctcacctca | cctgaggtcc | ggccgcccag | 60 |
| gggtgcgcta | tgccgtcggg | aggtgaccag | tcgccaccgc | ccccgcctcc | ccctccggcg | 120 |
| gcggcagcct | cggatgagga | ggaggaggac | gacggcgagg | cggaagacgc | cgcgccgtct | 180 |
| gccgagtcgc | ccacccctca | gatccagcag | cggttcgacg | agctgtgcag | ccgcctcaac | 240 |
| atggacgagg | cggcgcggcc | cgaggcctgg | gacagctacc | gcagcatgag | cgaaagctac | 300 |
| acgctggagg | gaaatgatct | tcattggtta | gcatgtgcct | tatatgtggc | ttgcagaaaa | 360 |
| tctgttccaa | ctgtaagcaa | agggacagtg | gaaggaaact | atgtatcttt | aactagaatc | 420 |
| ctgaaatgtt | cagagcagag | cttaatcgaa | tttttttaata | agatgaagaa | gtgggaagac | 480 |
| atggcaaatc | taccccccaca | tttcagaaa | cgtactgaga | gattagaaag | aaacttcact | 540 |
| gtttctgctg | taattttttaa | gaaatatgaa | cccattttttc | aggacatctt | taaatacccct | 600 |
| caagaggagc | aacctcgtca | gcagcgagga | aggaaacagc | ggcgacagcc | ctgtactgtg | 660 |
| tctgaaattt | tccattttttg | ttgggtgctt | tttatatatg | caaaaggtaa | tttccccatg | 720 |
| attagtgatg | atttggtcaa | ttcttatcac | ctgctgctgt | gtgctttgga | cttagtttat | 780 |
| ggaaatgcac | ttcagtgttc | taatcgtaaa | gaacttgtga | accctaattt | taaaggctta | 840 |
| tctgaagatt | ttcatgctaa | agattctaaa | ccttcctctg | accccccttg | tatcattgag | 900 |
| aaactgtgtt | ccttacatga | tggcctagtt | ttggaagcaa | aggggataaa | ggaacatttc | 960 |
| tggaaaccct | atattaggaa | actttatgaa | aaaaagctcc | ttaagggaaa | agaagaaaat | 1020 |
| ctcactgggt | ttctagaacc | tgggaacttt | ggagagagtt | ttaaagccat | caataaggcc | 1080 |
| tatgaggagt | atgttttatc | tgttgggaat | ttagatgagc | ggatatttct | tggagaggat | 1140 |
| gctgaggagg | aaattgggac | tctctcaagg | tgtctgaacg | ctggttcagg | aacagagact | 1200 |
| gctgaaaggg | tgcagatgaa | aaacatctta | cagcagcatt | ttgacaagtc | caaagcactt | 1260 |
| agaatctcca | caccactaac | tggtgttagg | tacattaagg | agaatagccc | ttgtgtgact | 1320 |
| ccagttttcta | cagctacgca | tagcttgagt | cgtcttcaca | ccatgctgac | aggcctcagg | 1380 |

```
aatgcaccaa gtgagaaact ggaacagatt ctcaggacat gttccagaga tccaacccag    1440
gctattgcta acagactgaa agaaatgttt gaaatatatt ctcagcattt ccagccagac    1500
gaggatttca gtaattgtgc taaagaaatt gccagcaaac attttcgttt tgcggagatg    1560
ctttactata aagtattaga atctgttatt gagcaggaac aaaaaagact aggagacatg    1620
gatttatctg gtattctgga acaagatgca ttccacagat ctctcttggc ctgctgcctt    1680
gaggtcgtca cttttctta taagcctcct gggaattttc catttattac tgaaatattt    1740
gatgtgcctc tttatcattt ttataaggtg atagaagtat tcattagagc agaagatggc    1800
ctttgtagag aggtggtaaa acaccttaat cagattgaag aacagatctt agatcatttg    1860
gcatggaaac cagagtctcc actctgggaa aaaattagag acaatgaaaa cagagttcct    1920
acatgtgaag aggtcatgcc acctcagaac ctggaaaggg cagatgaaat ttgcattgct    1980
ggctcccctt tgactcccag aagggtgact gaagttcgtg ctgatactgg aggacttgga    2040
aggagcataa catctccaac cacattatac gataggtaca gctcccccac agccagcact    2100
accagaaggc ggctatttgt tgagaatgat agcccctctg atggagggac gcctgggcgc    2160
atgcccccac agcccctagt caatgctgtc cctgtgcaga atgtatctgg ggagactgtt    2220
tctgtcacac cagttcctgg acagactttg gtcaccatgg caaccgccac tgtcacagcc    2280
aacaatggga aaacggtaac cattcctgtg caaggtattg ccaatgaaaa tggagggata    2340
acattcttcc ctgtccaagt caatgttggg gggcaggcac aagctgtgac aggctccatc    2400
cagcccctca gtgctcaggc cctggctgga agtctgagct tcaacaggt gacaggaaca    2460 actttgcaag tccctggtca gtggccatt caacagattt ccccaggtgg ccaacagcag    2520
aagcaaggcc agtctgtaac cagcagtagt aatagaccca ggaagaccag ctctttatcg    2580
cttttcttta gaaaggtata ccatttagca gctgtccgcc ttcgggatct ctgtgccaaa    2640
ctagatattt cagatgaatt gaggaaaaaa atctggacct gctttgaatt ctccataatt    2700
cagtgtcctg aacttatgat ggacagacat ctggaccagt tattaatgtg tgccatttat    2760
gtgatggcaa aggtcacaaa agaagataag tccttccaga acattatgcg ttgttatagg    2820
actcagccgc aggcccggag ccaggtgtat agaagtgttt tgataaaagg gaaaagaaaa    2880
agaagaaatt ctggcagcag tgatagcaga agccatcaga attctccaac agaactaaac    2940
aaagatagaa ccagtagaga ctccagtcca gttatgaggt caagcagcac cttgccagtt    3000
ccacagccca gcagtgctcc tcccacacct actcgcctca caggtgccaa cagtgacatg    3060
gaagaagagg agagggggaga cctcattcag ttctacaaca acatctacat caaacagatt    3120
aagacatttg ccatgaagta ctcacaggca aatatggatg ctcctccact ctctccctat    3180
ccatttgtaa aacaggctc ccctcgccga atacagttgt ctcaaaatca tcctgtctac    3240
atttccccac ataaaaatga aacaatgctt tctcctcgag aaaagatttt ctattacttc    3300
agcaacagtc cttcaaagag actgagagaa attaatagta tgatacgcac aggagaaact    3360
cctactaaaa agagaggaat tcttttggaa gatggaagtg aatcacctgc aaaaagaatt    3420
tgcccagaaa atcattctgc cttattacgc cgtctccaag atgtagctaa tgaccgtggt    3480
tcccactgag gttagtctct tgtattaaac tcttcacaaa atctgtttag cagcagcctt    3540
taatgcatct agattatgga gcttttttcc ttaatccagc tgatgagtta cagcctgtta    3600
gtaacatgag gggacatttt ggtgagaaat gggacttaac tccttccagt gtccttagaa    3660
cattttaatt catcccaact gtctttttt ccctaccact cagtgattac tgtcaaggct    3720
gcttacaatc caaacttggg ttttttggctc tggcaaagct tttagaaata ctgcaagaaa    3780
```

-continued

```
tgatgtgtac ccaacgtgag cataggaggc ttctgttgac gtctccaaca gaagaactgt    3840
gtttcaagtt caatcctacc tgttttgtgg tcagctgtag tcctcataaa aagcaaaaca    3900
aaaattaggt attttgtcct aaaacacctg gtaggagtgt gtgatttttt gcattcctga    3960
caaaggagag cacacccagg tttggaggtc ctaggtcatt agccctcgtc tcccgttccc    4020
tttgtgcaca tcttccctct ccccattcgg tgtggtgcag tgtgaaaagt ccttgattgt    4080
tcgggtgtgc aatgtctgag tgaacctgta taagtggagg cactttaggg ctgtaaaatg    4140
catgattttg taacccagat tttgctgtat atttgtgata gcacttctta caatgtgaac    4200
tttattaaat acaaaacttc caggctaaac atccaatatt ttctttaatg cttttatatt    4260
tttttaaaat gttaaaaccc ctatagccac cttttgggaa tgttttaaat tctccagttt    4320
tttgttatat agggatcaac cagctaagaa aagattttaa gtcaagttga attgagggga    4380
ttaatatgaa aacttatgac ctcttccttt aggagggagt tatctaaaag aaatgtctat    4440
taaggtgata tatttaaaaa tattttgggg tgttcctggc agtttaaaaa aattggttgg    4500
agaatttagg tttttattag taccatagta ccatttatac aaattagaaa atgttattta    4560
acagctgaat tatctataca tatctttatt aatcactatt gttccagcag ttttcaagtc    4620
aaattaataa tcttattagg gagaaaattc aattgtaaat tgaatcagta taaacaaagt    4680
tactaggtaa cttcatattg ctgagagaaa tatggaactt acattgttca attagaatag    4740
tgttctcccc aaatatttat aaaacttctc aagatactgc tacgtgtaat tttatatgaa    4800
gataagtgta ttttcaata aagcatttat aaattaaaaa aaaaaaaaaa aaa           4853
```

<210> SEQ ID NO 2
<211> LENGTH: 1139
<212> TYPE: PRT
<213> ORGANISM: Homo sapiens

<400> SEQUENCE: 2

```
Met Pro Ser Gly Gly Asp Gln Ser Pro Pro Pro Pro Pro Pro Pro Pro
  1               5                  10                  15

Ala Ala Ala Ala Ser Asp Glu Glu Glu Asp Asp Gly Glu Ala Glu
             20                  25                  30

Asp Ala Ala Pro Ser Ala Glu Ser Pro Thr Pro Gln Ile Gln Gln Arg
         35                  40                  45

Phe Asp Glu Leu Cys Ser Arg Leu Asn Met Asp Glu Ala Ala Arg Pro
     50                  55                  60

Glu Ala Trp Asp Ser Tyr Arg Ser Met Ser Glu Ser Tyr Thr Leu Glu
 65                  70                  75                  80

Gly Asn Asp Leu His Trp Leu Ala Cys Ala Leu Tyr Val Ala Cys Arg
                 85                  90                  95

Lys Ser Val Pro Thr Val Ser Lys Gly Thr Val Glu Gly Asn Tyr Val
            100                 105                 110

Ser Leu Thr Arg Ile Leu Lys Cys Ser Glu Gln Ser Leu Ile Glu Phe
        115                 120                 125

Phe Asn Lys Met Lys Lys Trp Glu Asp Met Ala Asn Leu Pro Pro His
    130                 135                 140

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
                165                 170                 175

Pro Gln Glu Glu Gln Pro Arg Gln Gln Arg Gly Arg Lys Gln Arg Arg
```

-continued

```
                180                 185                 190
Gln Pro Cys Thr Val Ser Glu Ile Phe His Phe Cys Trp Val Leu Phe
        195                 200                 205
Ile Tyr Ala Lys Gly Asn Phe Pro Met Ile Ser Asp Asp Leu Val Asn
210                 215                 220
Ser Tyr His Leu Leu Leu Cys Ala Leu Asp Leu Val Tyr Gly Asn Ala
225                 230                 235                 240
Leu Gln Cys Ser Asn Arg Lys Glu Leu Val Asn Pro Asn Phe Lys Gly
                245                 250                 255
Leu Ser Glu Asp Phe His Ala Lys Asp Ser Lys Pro Ser Ser Asp Pro
            260                 265                 270
Pro Cys Ile Ile Glu Lys Leu Cys Ser Leu His Asp Gly Leu Val Leu
        275                 280                 285
Glu Ala Lys Gly Ile Lys Glu His Phe Trp Lys Pro Tyr Ile Arg Lys
    290                 295                 300
Leu Tyr Glu Lys Lys Leu Lys Gly Lys Glu Asn Leu Thr Gly
305                 310                 315                 320
Phe Leu Glu Pro Gly Asn Phe Gly Glu Ser Phe Lys Ala Ile Asn Lys
                325                 330                 335
Ala Tyr Glu Glu Tyr Val Leu Ser Val Gly Asn Leu Asp Glu Arg Ile
            340                 345                 350
Phe Leu Gly Glu Asp Ala Glu Glu Ile Gly Thr Leu Ser Arg Cys
        355                 360                 365
Leu Asn Ala Gly Ser Gly Thr Glu Thr Ala Glu Arg Val Gln Met Lys
    370                 375                 380
Asn Ile Leu Gln Gln His Phe Asp Lys Ser Lys Ala Leu Arg Ile Ser
385                 390                 395                 400
Thr Pro Leu Thr Gly Val Arg Tyr Ile Lys Glu Asn Ser Pro Cys Val
                405                 410                 415
Thr Pro Val Ser Thr Ala Thr His Ser Leu Ser Arg Leu His Thr Met
            420                 425                 430
Leu Thr Gly Leu Arg Asn Ala Pro Ser Glu Lys Leu Glu Gln Ile Leu
        435                 440                 445
Arg Thr Cys Ser Arg Asp Pro Thr Gln Ala Ile Ala Asn Arg Leu Lys
    450                 455                 460
Glu Met Phe Glu Ile Tyr Ser Gln His Phe Gln Pro Asp Glu Asp Phe
465                 470                 475                 480
Ser Asn Cys Ala Lys Glu Ile Ala Ser Lys His Phe Arg Phe Ala Glu
                485                 490                 495
Met Leu Tyr Tyr Lys Val Leu Glu Ser Val Ile Glu Gln Gln Lys
            500                 505                 510
Arg Leu Gly Asp Met Asp Leu Ser Gly Ile Leu Glu Gln Asp Ala Phe
        515                 520                 525
His Arg Ser Leu Leu Ala Cys Cys Leu Glu Val Val Thr Phe Ser Tyr
    530                 535                 540
Lys Pro Pro Gly Asn Phe Pro Phe Ile Thr Glu Ile Phe Asp Val Pro
545                 550                 555                 560
Leu Tyr His Phe Tyr Lys Val Ile Glu Val Phe Ile Arg Ala Glu Asp
                565                 570                 575
Gly Leu Cys Arg Glu Val Val Lys His Leu Asn Gln Ile Glu Glu Gln
            580                 585                 590
Ile Leu Asp His Leu Ala Trp Lys Pro Glu Ser Pro Leu Trp Glu Lys
        595                 600                 605
```

-continued

```
Ile Arg Asp Asn Glu Asn Arg Val Pro Thr Cys Glu Val Met Pro
    610                 615                 620

Pro Gln Asn Leu Glu Arg Ala Asp Glu Ile Cys Ile Ala Gly Ser Pro
625                 630                 635                 640

Leu Thr Pro Arg Arg Val Thr Glu Val Arg Ala Asp Thr Gly Gly Leu
                645                 650                 655

Gly Arg Ser Ile Thr Ser Pro Thr Thr Leu Tyr Asp Arg Tyr Ser Ser
                660                 665                 670

Pro Pro Ala Ser Thr Thr Arg Arg Leu Phe Val Glu Asn Asp Ser
                675                 680                 685

Pro Ser Asp Gly Gly Thr Pro Gly Arg Met Pro Pro Gln Pro Leu Val
690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
                725                 730                 735

Ala Asn Asn Gly Gln Thr Val Thr Ile Pro Val Gln Gly Ile Ala Asn
                740                 745                 750

Glu Asn Gly Gly Ile Thr Phe Phe Pro Val Gln Val Asn Val Gly Gly
                755                 760                 765

Gln Ala Gln Ala Val Thr Gly Ser Ile Gln Pro Leu Ser Ala Gln Ala
770                 775                 780

Leu Ala Gly Ser Leu Ser Ser Gln Gln Val Thr Gly Thr Thr Leu Gln
785                 790                 795                 800

Val Pro Gly Gln Val Ala Ile Gln Ile Ser Pro Gly Gly Gln Gln
                805                 810                 815

Gln Lys Gln Gly Gln Ser Val Thr Ser Ser Asn Arg Pro Arg Lys
                820                 825                 830

Thr Ser Ser Leu Ser Leu Phe Phe Arg Lys Val Tyr His Leu Ala Ala
                835                 840                 845

Val Arg Leu Arg Asp Leu Cys Ala Lys Leu Asp Ile Ser Asp Glu Leu
850                 855                 860

Arg Lys Lys Ile Trp Thr Cys Phe Glu Phe Ser Ile Ile Gln Cys Pro
865                 870                 875                 880

Glu Leu Met Met Asp Arg His Leu Asp Gln Leu Leu Met Cys Ala Ile
                885                 890                 895

Tyr Val Met Ala Lys Val Thr Lys Glu Asp Lys Ser Phe Gln Asn Ile
                900                 905                 910

Met Arg Cys Tyr Arg Thr Gln Pro Gln Ala Arg Ser Gln Val Tyr Arg
                915                 920                 925

Ser Val Leu Ile Lys Gly Lys Arg Lys Arg Arg Asn Ser Gly Ser Ser
                930                 935                 940

Asp Ser Arg Ser His Gln Asn Ser Pro Thr Glu Leu Asn Lys Asp Arg
945                 950                 955                 960

Thr Ser Arg Asp Ser Ser Pro Val Met Arg Ser Ser Ser Thr Leu Pro
                965                 970                 975

Val Pro Gln Pro Ser Ser Ala Pro Pro Thr Pro Thr Arg Leu Thr Gly
                980                 985                 990

Ala Asn Ser Asp Met Glu Glu Glu Arg Gly Asp Leu Ile Gln Phe
                995                 1000                1005

Tyr Asn Asn Ile Tyr Ile Lys Gln Ile Lys Thr Phe Ala Met Lys Tyr
    1010                1015                1020
```

-continued

Ser Gln Ala Asn Met Asp Ala Pro Pro Leu Ser Pro Tyr Pro Phe Val
1025                1030                1035                1040

Arg Thr Gly Ser Pro Arg Arg Ile Gln Leu Ser Gln Asn His Pro Val
            1045                1050                1055

Tyr Ile Ser Pro His Lys Asn Glu Thr Met Leu Ser Pro Arg Glu Lys
        1060                1065                1070

Ile Phe Tyr Tyr Phe Ser Asn Ser Pro Ser Lys Arg Leu Arg Glu Ile
    1075                1080                1085

Asn Ser Met Ile Arg Thr Gly Glu Thr Pro Thr Lys Lys Arg Gly Ile
1090                1095                1100

Leu Leu Glu Asp Gly Ser Glu Ser Pro Ala Lys Arg Ile Cys Pro Glu
1105                1110                1115                1120

Asn His Ser Ala Leu Leu Arg Arg Leu Gln Asp Val Ala Asn Asp Arg
            1125                1130                1135

Gly Ser His

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
aaatttgtta gttggattag atcga                                        25

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
ttcaaaaaaa cctttaatta aaacg                                        25

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aaatttgtta gttggattag attga                                        25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
caaaaaaacc tttaattaaa acaca                                        25

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
aaacgacgaa cgctaaaccg aaaaaaaa                                28

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
aacaaacaac aaacactaaa ccaaaaaaaa a                             31

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
aggagctggc ggagggcgtt cg                                       22

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
agcgcatgtc ccgccgacac gc                                       22

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cgagcgctgg gccggggagg g                                        21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcccggcgc gcgccccgcc                                          20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
aggagctggc ggagggcgtt cg                                       22

<210> SEQ ID NO 14
<211> LENGTH: 22

-continued

```
<212> TYPE: DNA
<213> ORGANISM: Artificial Sequence
<220> FEATURE:
<223> OTHER INFORMATION: primer

<400> SEQUENCE: 14
agcgcatgtc ccgccgacac gc                                              22

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
cgagcgctgg gccggggagg g                                               21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ctcccggcgc gcgccccgcc                                                 20
```

METHODS OF DIAGNOSING, PROGNOSING AND TREATING BREAST CANCER

FIELD OF THE INVENTION

This invention relates to methods of diagnosing breast cancer, especially estrogen-insensitive breast cancer, to methods of determining the prognosis of subjects with breast cancer, and to methods of inhibiting the growth of estrogen-insensitive breast cancer cells. In particular, the methods of the invention involve measuring or inhibiting the activity of pRb2/p130, or determining the methylation state of the ER-α gene promoter and/or the presence of specific pRb2/p130-multimolecular complexes on the ER-α gene promoter in breast cancer cells.

BACKGROUND OF THE INVENTION

Many studies have identified oncogenes and tumor suppressor genes as markers of cellular transformation in several tissue types, such as colon, pancreas and lung, whereas comparable studies in breast cancer have met with limited success (West et al., 2001, Proc. Natl. Acad. Sci. USA, 98, 11462). This reflects the difficulty in finding genetic and epigenetic alterations in a significant proportion of breast cancers, and also underscores the phenotypic heterogeneity of breast cancer. The identification of molecular targets for early diagnosis of breast cancer could lead to improved diagnosis and treatment based on a molecular diagnosis.

Most mammary carcinomas contain estrogen receptors (ER), which are important factors for diagnosis and prognosis of breast cancer, and for determining therapeutic choices (Osborne, 1998, Breast Cancer Res. Treat., 51, 227). Estrogens are direct mitogens for hormone-responsive human breast cancer cells, where they promote cell cycle progression and induce the transcriptional activation of "immediate early" and cyclin genes. The estrogen receptor alpha (ER-α) and its ligand (17β-estradiol) play a crucial role in normal breast development, and have also been linked to mammary carcinogenesis and clinical outcome in breast cancer patients. However, up to one third of breast cancers lack ER-α at the time of diagnosis, and a fraction of breast cancers that are initially ER-α-positive lose ER during tumor progression (Hortobagyi, 1998, New Engl. J. Med., 339, 974). In a significant fraction of breast cancers, the absence of ER-α gene expression has been associated with the aberrant methylation of its CpG islands (Hortobagyi, 1998; Weigel and Coninck, 1993, Cancer Res., 53, 3472).

There is abundant evidence that the structure and chemical composition of chromatin directly affects gene expression. Histones are the primary structural components of chromatin. The nucleosome is the basic repeating unit of chromatin; further compaction of nucleosomes, with the aid of the histone H1 and other non-histone proteins, leads to a condensed chromatin state (Hayes and Hansen, 2001, Curr. Opin. Genet. Dev., 11, 124). The chromatin is thus made inaccessible to the transcriptional machinery, resulting in gene silencing.

Chromatin structure and function are controlled, at least in part, through post-translational modifications of nucleosomal histones. The core histone tails are susceptible to a variety of covalent modifications, including acetylation, methylation, phosphorylation and ubiquitination. Different studies collectively support the "histone code hypothesis" of histone modification (Strahl and Allis, 2000, Nature, 403, 41), which suggests that the presence of a given modification on histone tails may dictate or prevent the presence of a second modification elsewhere on the same histone. Histone modifications may therefore serve as marks for the recruitment of different proteins or protein complexes, which regulate chromatin functions such as gene expression.

DNA methylation is also important for transcriptional silencing. Therefore, it has been proposed that DNA methylation and histone deacetylation might work together to establish a repressive chromatin environment and silence gene expression (Cameron et al., 1999, Nat. Genet., 21, 103). For example, the formation of transcriptional repression complexes such as DNA methyltransferase 1 (DNMT1)/histone deacetylase (HDAC) is emerging as an important mechanism in gene expression regulation (Grunstein, 1997, Nature, 389, 349; Struhl, 1998, Genes & Dev. 12, 599; Lin et al., 1998, Nature, 391, 8311; Laird and Jaenisch, 1996, Annu. Rev. Genet. 30, 441). Aberrant recruitment of HDAC activity has also been associated with the development of certain human cancers (Nan et al., 1998, Nature, 393, 386) and changes in the patterns of CpG-methylation appear to be an intrinsic feature of human malignancy (Jones et al., 1998, Nat. Genet., 19, 187). However, the mechanisms of gene silencing by methylation remain poorly understood. Recent studies suggest that histone methylation, similar to histone deacetylation, might function in concert with DNA methylation (Bird and Wolffe, 1999, Cell, 99, 451), or that histone methylation on lysines by the histone methyl transferase SUV39H1 is important for transcriptional silencing. A specific chromatin structure involving methylated histones may also be necessary for DNA methylation to occur (Ng and Bird, 1999, Curr. Opin. Genet. Dev., 9, 158).

Several mechanisms have been proposed to account for transcriptional repression by the Rb proteins (Magnaghi-Jaulin et al., 1998, Nature, 391, 601; Dunaief et al., 1994, Cell, 79, 119, Trouche et al., 1997, Proc. Natl. Acad. Sci. USA, 94, 11268). Some of the proposed models stress the importance of chromatin structure in regulating transcriptional activity. Active repression by Rb family members could involve a mechanism by which condensed chromatin structure is enhanced through histone deacetylation and methylation. Rb proteins have been shown to repress E2F-dependent transcription by recruiting HDAC1/2 (Iavarone and Massague, 1999, Mol. Cell Biol., 19, 916; Stiegler et al., 1998, Cancer Res., 58, 5049). Recent data show that pRb2/p130 and p107 are able to interact physically with HDAC1 through the A/B pocket domains (Magnaghi-Jaulin et al., 1998; Iavarone and Massague, 1999; Ferreira et al., 1998, Proc. Natl. Acad. Sci. USA, 95, 10493).

Repression of E2F-responsive promoters in quiescent cells is associated with E2F-4 and pRb2/p130 recruitment and low histone acetylation levels. Recently, different studies have shown that SUV39H1 is involved in transcriptional repression by the retinoblastoma protein Rb1/p105 (Vandel et al., 2001, Mol. Cell. Biol., 21, 6484).

Chromatin inactivation mediated by histone deacetylation and DNA methylation are critical components of ER-α silencing in human breast cancer cells. In vitro studies have shown that DNMT1 interacts physically with either HDAC1 or 2, and that co-treatment with DNMT1 and HDAC inhibitors can synergistically induce ER-α gene expression in ER-α-negative breast cancer cells (Rountree et al., 2000, Nat. Genet., 25, 269; Robertson et al., 2000, Nat. Genet., 25, 338; Yang et al., 2001, Cancer Res., 60, 6890). However, the molecular factors which promote DNMT1 and HDAC interaction and otherwise regulate the ER-α gene expression have not heretofore been identified.

The ability to identify breast cancer patients with more aggressive diseases is crucial to an accurate prognosis and the planning of an adequate treatment. For example, those breast cancers which are estrogen-receptor negative (also called estrogen-insensitive breast cancers) have a higher malignant potential. Typically, metastatic potential is determined by considering a range of pathologic tumor features, including histologic type, grade of differentiation, depth of invasion, and extent of lymph nodal metastases. Unfortunately, these factors do not always allow a sufficiently accurate determination of metastatic potential of breast cancer. Such parameters also have questionable reproducibility. Estrogen-receptor negative breast cancers are also less susceptible to treatment with anticancer drugs such as tamoxifen.

What is needed, therefore, is a method of detecting and regulating the molecular factors which control ER-α gene expression, particularly in estrogen receptor-negative breast cancer cells. The detection and regulation of such factors would allow estrogen-insensitive breast cancer cells to be identified, so that an accurate prognosis can be obtained and an appropriate course of treatment administered. Also, detecting and regulating the molecular factors which control ER-α gene expression would allow estrogen-insensitive cells to be converted to estrogen-sensitive cells, which are generally more susceptible to current anti-cancer treatments.

SUMMARY OF THE INVENTION

The protein pRb2/p130 represses expression of the ER-α gene. Blocking pRb2/p130 activity or otherwise altering the proteins which bind to the ER-α gene in conjunction with pRb2/p130 allows transcriptional activity of the ER-α gene to be restored. In the case of estrogen receptor negative breast cancer cells, restoring transcriptional activity of the ER-α gene converts the cells to estrogen receptor-positive cells.

Without wishing to be bound by any theory, pRb2/p130 is believed to be associated with two multi-molecular complexes which bind to the ER-α promoter. Different physiologically important enzymes and transcription factors can be recruited by pRb2/p130 to the ER-α promoter. Again without wishing to be bound by any theory, the identity and temporal specificity of the recruited enzymes and transcription factors in the pRb2/p130 complexes likely control chromatin organization by inducing different acetylation and methylation levels. These different acylation and methylation levels in turn affect the transcriptional regulation of the ER-α gene.

Thus, the invention provides a method of diagnosing breast cancer, comprising the steps of obtaining a sample of breast cancer cells, and determining the DNA methylation pattern of the ER-α gene promoter and optionally the presence of specific pRb2/p130-multimolecular complexes on the ER-α gene promoter in those cells. The presence of DNA methylation in the A, B, C and E regions of the ER-α gene promoter; optionally together with the presence of pRb2/p130-E2F4/5-HDAC1-DNMT1-SUV39H1 multimolecular complex on the ER-α gene promoter, in the breast cancer cells indicates that the breast cancer cells are estrogen receptor-negative breast cancer cells. The presence of DNA methylation only in the D region of the ER-α gene promoter, optionally together with the presence of pRb2/p130-E2F4/5-HDAC1-SUV39H1-p300 multimolecular complex, indicates that the breast cancer cells are estrogen receptor-positive breast cancer cells.

The invention further provides a method of determining the prognosis of a subject suffering from breast cancer, comprising the steps of obtaining a sample of breast cancer cells from the subject, and determining the DNA methylation pattern of the ER-α gene promoter, and optionally determines the presence of specific pRb2/p130 multimolecular complexes on the ER-α gene promoter. The presence of DNA methylation in the A, B, C and E regions of the ER-α gene promoter, optionally together with the presence of pRb2/p130-E2F4/5-HDAC1-DNMT1-SUV39H1 multimolecular complex on the ER-α gene promoter, indicates that the breast cancer cells are estrogen receptor-negative. As estrogen receptor-negative breast cancer cells have a high metastatic potential, the subject therefore has an unfavorable prognosis. The presence of DNA methylation only in the D region of the ER-α gene promoter, optionally together with the presence of pRb2/p130-E2F4/5-HDAC1-SUV39H1-p300 multimolecular complex on the ER-α gene promoter, indicates that the breast cancer cells are estrogen receptor-positive, and that the subject has a more favorable prognosis.

The invention further provides a method of producing estrogen receptor-positive breast cancer cells, comprising the step of obtaining a sample of estrogen receptor-negative breast cancer cells and activating transcription of the ER-α gene in those cells. Transcriptional activation of the ER-α gene causes the estrogen receptor-negative breast cancer cells to become estrogen receptor-positive breast cancer cells.

The invention still further provides a method of treating estrogen receptor-negative breast cancer comprising the steps of providing a subject having estrogen receptor-negative breast cancer cells, and exposing the estrogen receptor-negative breast cancer cells to an effective amount of at least one compound that activates transcription of the ER-α gene. Transcriptional activation of the ER-α gene causes the estrogen receptor-negative breast cancer cells to become estrogen receptor-positive breast cancer cells. The subject can then undergo breast cancer therapy which targets estrogen receptor-positive breast cancer cells.

The invention still further provides the use of a compound which activates transcription of the ER-α gene, for the production of a medicament for the treatment of estrogen receptor-negative breast cancer.

BRIEF DESCRIPTION OF THE FIGURES

FIGS. 1a-1d show methylation analyses of ER-α promoter in: FIG. 1a, MDA-MB-231 breast cancer cell line. (U); FIG. 1b, MCF-7 breast cancer cell line; FIG. 1c, five primary breast tumors. FIG. 1d, Methylation analysis of ER-β promoter in MDA-MB-231 and MCF-7 cell lines. C1 and C2 are the negative and positive controls, respectively.

FIG. 2a, Western blot of chromatin immunoprecipitated after cross-linking (pRb2/p130 was used as the immunoprecipitating antibody) using antibodies against E2F4, E2F5, HDAC1, SUV39H1, p300 and DNMT1. FIG. 2b, DNA extracted from the immunoprecipitates of a and amplified by PCR using specific primers spanning ER-α and ER-β promoter fragments. The input represents the cross-linked chromatin before the immunoprecipitation. FIG. 2c, Direct sequencing chromatogram of one of the PCR products shown in b. FIG. 2d, XChIP analyses using E2F4, E2F5, HDAC1, SUV39H1, p300 and DNMT1 as immunoprecipitating antibodies, and PCR results using the same primers spanning ER-α as those described in FIG. 2b.

FIG. 4a, pRb2/p130 recruits histone deacetylase 1 (HDAC1), histone methyl transferase (SUV39H1) and histone acetyl transferase (HAT or p300) in multimolecular complexes on the ER-α promoter, in MCF-7 cells; FIG. 4b, recruitment of DNA methyl transferase 1 (DNMT1) and concomitant release of HAT from the multimolecular complexes.

FIG. 5a, ER-α RNA was detected with RT-PCR in total RNA preparation from MDA-MB-231 cells grown in DMEM medium at the density of $5 \times 10^5$ cells/100-mm plate untreated or treated with 2.5 µM 5-Aza-2-deoxicytidine (5-Aza-2dC) for 24, 36, 48, 72, and 96 hours. β-actin RNA expression was determined in each sample by RT-PCR to normalize RNA loading; FIG. 5b, ER-α protein detected by Western blotting using whole lysates from MDA-MB-231 cells untreated or treated with 2.5 µM 5-Aza-2dC for 24, 36, 48, 72, and 96 hours. The expression of β-actin protein in each sample was assessed to normalize protein loading.

FIG. 7a shows the components and assembly of the pRb2/p130 multimolecular complex bound to the ER-α promoter before 5-Aza-2dC treatment. FIG. 7b shows that the treatment of MDA-MB-231 cells with 5-Aza-2dC induces the re-expression of ER-α by causing the reorganization of the pRb2/p130 multimolecular complex bound to ER-α promoter.

DETAILED DESCRIPTION OF THE INVENTION

The ER-α gene plays a crucial role in normal breast development and is also linked to development and progression of mammary carcinoma (Osborne, 1998; Hortobagyi, 1998; Yang, 2001). Without wishing to be bound by any theory, it is believed that transcriptional repression of the ER-α gene is mediated by pRb2/p130 in ER-negative breast cancer cells via two complexes: pRb2/p130-E2F4/5-HDAC1-SUV39H1-p300 and pRb2/p130-E2F4/5-HDAC1-DNMT1-SUV39H1. These pRb2/p130 complexes appear to provide a link between pRb2/p130 and chromatin-modifying enzymes in the regulation of ER-α gene transcription in a physiological setting. The identity and temporal specificity of recruited enzymes and transcription factors in either pRb2/p130 complex can control chromatin organization by inducing different histone acetylation and methylation levels. These different acetylation and methylation levels affect the accessibility of the ER-α gene to the basal transcription machinery.

Figure 4A:
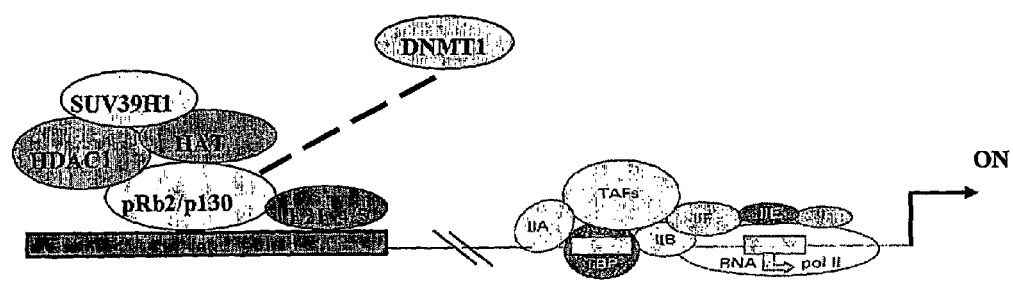
FIGS. 4a-4b illustrate a proposed model of pRb2/p130 regulation of ER-α transcription.
Figure 4B:
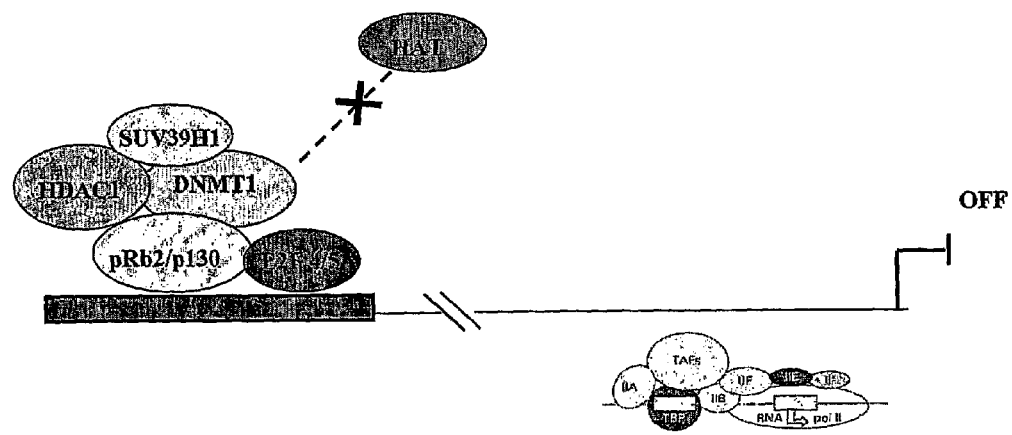

For example, the recruitment of SUV39H1, HDAC1 and p300 by pRb2/p130 regulates expression of the ER-α in estrogen receptor-positive MCF-7 breast cancer cells, and further recruitment of DNMT1 (with the concomitant release of p300/CBP) could be required for long-term ER-α gene silencing in estrogen receptor-negative MDA-MB-231 breast cancer cells (see FIGS. 4a and b). pRb2/p130 is described in GenBank record Accession No. NM_005611 and Tedesco D et al., Genes Dev. 16 (22), 2946-2957, 2002, the entire disclosures of which is herein incorporated by reference. The cDNA sequence of pRb2/p130 is given herein as SEQ ID NO: 1, and the corresponding pRb2/p130 amino acid sequence is given herein as SEQ ID NO: 2.

Thus, breast cancer cell type can be identified on the basis of DNA methylation patterns in the ER-α gene promoter, which indicates whether the ER-α gene has undergone transcriptional repression by the pRb2/p130 protein. DNA methylation in the A, B, C, and E regions of the ER-α gene promoter indicate that the gene is transcriptionally repressed, and no ER-α is being produced. Thus, a breast cancer cell which exhibits DNA methylation in the A, B, C, and E regions of the ER-α gene promoter is an estrogen-receptor negative breast cancer cell. Breast cancer cells which exhibit no DNA methylation in the ER-α gene promoter, or DNA methylation only in the D region of the ER-α gene promoter, are estrogen receptor-positive because the ER-α gene is not transcriptionally repressed in such cells.

In a preferred embodiment, breast cancer cell type can be identified on the basis of DNA methylation patterns in the ER-α gene promoter together with the detection of the presence of specific pRb2/p130-multimolecular complexes on the ER-α gene promoter. In this preferred embodiment, DNA methylation in the A, B, C, and E regions of the ER-α gene promoter, together with the presence of pRb2/p130-E2F4/5-HDAC1-DNMT1-SUV39H1 complex, indicate that the ER-α gene is transcriptionally repressed and no ER-α is being produced. No DNA methylation in the ER-α gene promoter, or DNA methylation only in the D region of the ER-α gene promoter, together with the presence of pRb2/p130-E2F4/5-HDAC1-SUV39H1-p300 indicates that the ER-α gene is not transcriptionally repressed and that the breast cancer cell is estrogen receptor-positive. Methods for determining the methylation pattern of the ER-α gene and the presence of specific pRb2/p130 multimolecular complexes on the ER-α gene promoter the within the skill in the art, and representative techniques are given in the Examples below.

One skilled in the art would understand that methylation in a given region of the ER-α gene promoter occurs at each cytosine in that region of the ER-α gene promoter sequence which is followed by a guanosine in the 3'-direction; i.e., the sequence 5'-CG-3'). Thus, "the presence of methylation in a region of the ER-α gene promoter" means that the available 5'-CG-3' methylation sites in that ER-α gene promoter are methylated. Methods for determining the methylation pattern of the ER-α gene are within the skill in the art, and representative techniques are given in the Examples below.

The presence of breast cancer cells of a certain type in a subject is diagnostic of breast cancer of that type. That is, if estrogen receptor-positive breast cancer cells are present, then the subject is suffering from estrogen receptor-positive breast cancer. If estrogen receptor-negative breast cancer cells are present, then the subject is suffering from estrogen receptor-negative breast cancer.

"Expression," with respect to a gene, means the realization of genetic information encoded in the gene to produce a functional RNA or protein. The term is thus used in its broadest sense, unless indicated to the contrary, to include either transcription or translation, as well as activity of the mature protein product of a gene. Thus, a blocking or absence of pRb2/p130 protein activity in a cell (for example, if the pRb2/p130 protein is mutated) would be considered "inhibition of pRb2/p130 expression." The inhibition of pRb2/p130 expression can lead to the re-expression of ER-α in ER-negative breast cancer cells.

Cell or tissue samples for use in the present methods can be obtained by standard techniques, such as punch or needle biopsy, surgical biopsy, and the like. For example, a test sample of tissue or cells from a subject suspected of having breast cancer is obtained by surgical biopsy. As a control, a tissue or cell sample from unaffected breast tissues of the subject, or from a normal subject, is also obtained. Genomic DNA can then be isolated from the test and control samples using standard techniques, for determination of ER-α gene promoter methylation levels.

Subjects suffering from estrogen receptor-positive breast cancer have a more favorable prognosis than subjects suffering from estrogen receptor-negative breast cancer. Generally, estrogen receptor-positive breast cancer is not refractory to treatment with anti-estrogen cancer therapeutics such as tamoxifen, toremifene, or raloxifene. In contrast, subjects suffering from estrogen receptor-negative breast cancer have a poor prognosis, as this form of breast cancer is known to have a high metastatic potential and is generally resistant to anti-estrogen therapeutics. In the practice of the present invention, the prognosis of a subject suffering from breast cancer can be determined by evaluating whether breast cancer cells in the subject are estrogen receptor-positive or estrogen receptor-negative, as described above.

Inhibition of pRb2/p130 expression in estrogen receptor-negative breast cancer cells removes the transcriptional repression of the ER-α gene, which then becomes transcriptionally active and produces ER-α in the cell. Activation of ER-α gene transcription can also be accomplished by altering the methylation pattern of the ER-α gene promoter, for example by targeting the DNMT1 activity in the pRb2/p130-E2F4/5-HDAC1-DNMT1-SUV39H1 complex. Breast cancer cells which are initially ER-negative can therefore be converted into ER-positive breast cancer cells by activating transcription of the ER-α gene. Because ER-α is now being produced in such cells from the transcriptionally active ER-α gene, such cells can be classified as estrogen receptor-positive breast cancer cells. As discussed above, estrogen receptor-positive breast cancer cells have a lower malignant potential than estrogen receptor-negative breast cancer cells, and are less refractory to anti-estrogen therapeutics such as tamoxifen.

In a preferred embodiment, estrogen receptor-positive breast cancer cells are produced from estrogen receptor-negative breast cancer cells by inhibiting expression or activity of pRb2/p130 in the cells, such that the ER-α gene is transcriptionally active. pRb2/p130 expression can be inhibited at either the RNA level, the protein level, or both. As used herein, "inhibition of gene expression at the RNA level" refers to the prevention of transcription or translation of an RNA transcript into a protein product, including the use of antisense oligonucleotides or induction of RNA interference. As used herein, "inhibition of gene expression at the protein level" refers to the complete or partial blockage of protein function, including by degradation of the protein, or binding of the protein by an antibody or aptamer.

pRb2/p130 expression can be inhibited by any suitable technique known to one of ordinary skill in the art. For example, pRb2/p130 expression can be inhibited by administering antisense oligonucleotides designed to target the pRb2/p130 mRNA (e.g., SEQ ID NO: 1). The pRb2/p130 targetcan be single-stranded or double-stranded DNA or RNA; however, single-stranded DNA or RNA targets are preferred, with single-stranded mRNA targets being particularly preferred. It is understood that the target to which the pRb2/p130 antisense oligonucleotides of the invention are directed include allelic forms of pRb2/p130. In particular, the invention contemplates the targeting of the specific pRb2/p130 allele or alleles in a given subject, which alleles can be determined by standard molecular biology techniques. The targeting of a subject-specific pRb2/p130 allele allows for the so-called "personalized treatment" of the subject's cancer, which may prove highly effective in combating the disease in a given individual.

There is substantial guidance in the literature for selecting particular sequences for antisense oligonucleotides given a knowledge of the sequence of the target polynucleotide; e.g., Peyman and Ulmann, 1990, Chemical Reviews, 90, 543; Crooke, 1992, Ann. Rev. Pharmacal. Toxicol., 32, 329; and Zamecnik and Stephenson, Proc. Natl. Acad. Sci., 75, 280, the entire disclosures of which are herein incorporated by reference. Preferably, the sequences of pRb2/p130 antisense compounds are selected such that the G-C content is at least 60%. Preferred pRb2/p130 mRNA targets include the 5' cap site, tRNA primer binding site, the initiation codon site, the mRNA donor splice site, and the mRNA acceptor splice site; see, e.g., Goodchild et al., U.S. Pat. No. 4,806,463, the entire disclosure of which is herein incorporated by reference.

Where the target polynucleotide comprises a pRb2/p130 mRNA transcript, oligonucleotides complementary to any portion of the transcript are, in principle, effective for inhibiting translation and capable of inducing the effects herein described. It is believed that translation is most effectively inhibited by blocking the mRNA at a site at or near the initiation codon. Thus, oligonucleotides complementary to the 5'-region of the pRb2/p130 mRNA transcript are preferred. Oligonucleotides complementary to the pRb2/p130 mRNA, including the initiation codon (the first codon at the 5' end of the translated portion of the pRb2/p130 transcript), or codons adjacent the initiation codon, are preferred.

While antisense oligonucleotides complementary to the 5'-region of the pRb2/p130 transcript are preferred, particularly the region including the initiation codon, it should be appreciated that useful antisense oligomers are not limited to those complementary to the sequences found in the translated portion of the mRNA transcript, but also include oligomers complementary to nucleotide sequences contained in, or extending into, the 5'- and 3'-untranslated regions of the mRNA transcript.

Antisense oligonucleotides of the invention can comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention can also contain pendent groups or moieties, either as part of or separate from the basic repeat unit of the polymer, to enhance specificity, nuclease resistance, delivery, or other property related to efficacy; e.g., cholesterol moieties, duplex intercalators such as acridine, poly-L-lysine, "end-capping" with one or more nuclease-resistant linkage groups such as phosphorothioate, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligo-nucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligo-nucleosides is disclosed in Tso et al., U.S. Pat. No. 4,469,863.

Preferably, nuclease resistance is conferred on the antisense compounds of the invention by providing nuclease-resistant internucleosidic linkages. Many such linkages are known in the art; e.g., phosphorothioate: Zon and Geyser, 1991, *Anti-Cancer Drug Design*, 6:539; Stec et al., U.S. Pat. No. 5,151,510; Hirschbein, U.S. Pat. No. 5,166,387; Bergot, U.S. Pat. No. 5,183,885; phosphorodithioates: Marshall et al., 1993, *Science*, 259, 1564; Caruthers and Nielsen, International application PCT/US89/-02293; phosphoramidates, e.g., —OP(=O)(NR$^1$R$^2$)—O— with R$^1$ and R$^2$ hydrogen or $C_1$-$C_3$ alkyl; Jager et al., 1988, *Biochemistry*, 27, 7237; Froehler et al., International application PCT/US90/03138; peptide nucleic acids: Nielsen et al., 1993, *Anti-Cancer Drug Design*, 8, 53; International application PCT/EP92/01220; methylphosphonates: Miller et al., U.S. Pat. No. 4,507,433, Ts'o et al., U.S. Pat. No. 4,469,863; Miller et al., U.S. Pat. No. 4,757,055; and P-chiral linkages of various types, especially phosphorothioates, Stec et al., European patent application 506,242 (1992) and Lesnikowski, *Bioorganic Chemistry*, 21, 127. Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thiofornacetal, silyl such as dialkyl($C_1$-$C_6$)— or diphenylsilyl, sulfamate ester, and the like. Such linkages and methods for introducing them into oligonucleotides are described in many references; e.g., reviewed generally by Peyman and Ulmann, 1990, *Chemical Reviews* 90:543; Milligan et al., 1993, *J. Med. Chem.*, 36, 1923; Matteucci et al., International application PCT/US91/06855. The entire disclosures of all documents referred to in this paragraph are herein incorporated by reference.

Resistance to nuclease digestion may also be achieved by modifying the internucleotide linkage at both the 5' and 3' termini with phosphoroamidites according to the procedure of Dagle et al., 1990, *Nucl. Acids Res*. 18, 4751, the entire disclosure of which is herein incorporated by reference.

Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (see Loke et al., 1989, *Proc. Natl. Acad. Sci.*, 86, 3474, the entire disclosure of which is herein incorporated by reference).

It is understood that in addition to the preferred linkage groups, antisense compounds of the invention can comprise additional modifications; e.g., boronated bases (see, e.g., Spielvogel et al., U.S. Pat. No. 5,130,302); cholesterol moieties (see, e.g., Shea et al., 1990, *Nucl. Acids Res*., 18, 3777 or Letsinger et al., 1989, *Proc. Natl. Acad Sci. USA*, 86, 6553); and 5-propynyl modification of pyrimidines (see, e.g., Froehler et al., 1992, *Tetrahedron Lett*., 33, 5307). The entire disclosures of all documents referred to in this paragraph are herein incorporated by reference.

Preferably, antisense compounds of the invention are synthesized by conventional means on commercially available automated DNA synthesizers; e.g., an Applied Biosystems (Foster City, Calif.) model 380B, 392 or 394 DNA/RNA synthesizer. Preferably, phosphoramidite chemistry is employed e.g., as disclosed in the following references: Beaucage and Iyer, 1992, *Tetrahedron*, 48, 2223; Molko et al., U.S. Pat. No. 4,980,460; Koster et al., U.S. Pat. No. 4,725,677; Caruthers et al., U.S. Pat. Nos. 4,415,732; 4,458,066; and 4,973,679, the entire disclosures of which are herein incorporated by reference.

In embodiments where triplex nucleic acid formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and anti-parallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments; see, e.g., Roberts et al., 1991, *Proc. Natl. Acad. Sci. USA*, 88, 9397; Roberts et al., 1992, *Science*, 258, 1463; Distefano et al., 1993, *Proc. Natl. Acad. Sci. USA*, 90, 1179; Mergny et al., *Biochemistry*, 30, 9791-9798 (1992); Cheng et al., J. Am. Chem. Soc., 114:4465-4474 (1992); Beal and Dervan, Nucleic Acids Research, 20:2773-2776 (1992); Beal and Dervan, J. Am. Chem. Soc., 114:4976-4982; Giovannangeli et al., Proc. Natl. Acad. Sci., 89:8631-8635 (1992); Moser and Dervan, Science, 238:645-650 (1.987); McShan et al., J. Biol. Chem., 267: 5712-5721 (1992); Yoon et al., Proc. Natl. Acad. Sci., 89:3840-3844 (1992); and Blume et al., Nucleic Acids Research, 20:1777-1784 (1992), the entire disclosures of which are herein incorporated by reference.

The length of the antisense oligonucleotides should be sufficiently large to ensure that specific binding will take place only at the desired target polynucleotide and not at other fortuitous sites, as explained in many references; e.g., Rosenberg et al., International application PCT/US92/05305; or Szostak et al., 1979, *Meth. Enzymol.*, 68, 419. The upper range of the length is determined by several factors, including the inconvenience and expense of synthesizing and purifying oligomers greater than about 30-40 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

In general, the antisense oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g., the pRb2/p130 mRNA) is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch probably will not be tolerated for antisense oligomers of less than about 21 nucleotides. One skilled in the art can readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0-2.0 μM. Typical conditions are as follows: 150 mM NaCl and 10 mM $MgCl_2$ in a 10 mM sodium phosphate buffer (pH 7.0) or in a 10 mM Tris-HCl buffer (pH 7.0). Data for melting curves are accumulated by heating a sample of the antisense oligonucleotide/target polynucleotide complex from room temperature to about 85-90° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

pRb2/p130 expression can also be inhibited by "RNA interference" or "RNAi." RNAi is a method of post-transcriptional gene regulation that is conserved throughout many eukaryotic organisms. RNAi is induced by short (i.e., <30 nucleotide) double stranded RNA ("dsRNA") molecules (Fire A et al. (1998), *Nature* 391: 806-811). These short dsRNA molecules, called "short interfering RNA" or "siRNA," cause the destruction of RNAs which share sequence homology with the siRNA to within one nucleotide resolution (Elbashir S M et al. (2001), *Genes Dev*, 15: 188-200). It is believed that the siRNA and the targeted RNA bind to an "RNA-induced silencing complex" or "RISC", which cleaves the targeted RNA. The siRNA is apparently recycled much like a multiple-turnover enzyme, with one siRNA molecule capable of inducing cleavage of approximately 1000 RNA molecules. siRNA-mediated RNAi degradation of an RNA is therefore more effective than currently available technologies for inhibiting expression of a target gene. The specificity of siRNA-induced RNAi allows the targeting of subject-specific pRb2/p130 alleles, so that "personalized treatment" of the subject's breast cancer can be performed.

The siRNA of the invention comprise short double-stranded RNA from about 17 nucleotides to about 29 nucleotides in length, preferably from about 19 to about 25 nucleotides in length, that are targeted to the SEQ ID NO: 1. The siRNA's comprise a sense RNA strand and a complementary antisense RNA strand annealed together by standard Watson-Crick base-pairing interactions (hereinafter "base-paired"). As is described in more detail below, the sense strand comprises a nucleic acid sequence which is identical to a target sequence contained within the target RNA. As mentioned above, the target RNA can be any pRb2/p130 allele, for example SEQ ID NO: 1 or an allele isolated from a given subject.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules (see Tuschl, T. (2002), supra).

As used herein, an "isolated" molecule is a molecule which is synthetic, or which is altered or removed from the natural state through human intervention. For example, an siRNA naturally present in a living animal is not "isolated," but a synthetic siRNA, or an siRNA which is partially or completely separated from the coexisting materials of its natural state, is "isolated." An isolated siRNA can exist in substantially purified form, or can exist in a non-native environment such as, for example, a cell into which the siRNA has been introduced. Molecules which are produced inside a cell by natural processes, but which are produced from an "isolated" precursor molecule, are also considered to be "isolated" molecules. For example, an isolated double-stranded RNA (dsRNA) can be introduced into a target cell, where it is processed by the Dicer protein (or its equivalent) into siRNA. The siRNA produced from the original isolated dsRNA inside the cell are isolated molecules for purposes of the present invention. RNA transcripts produced from an expression vector inside a cell are also considered to be "isolated" molecules.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA of the invention can also comprise a 3' overhang. As used herein, a "3' overhang" refers to at least one unpaired nucleotide extending from the 3'-end of an RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

The siRNA of the invention can be targeted to any stretch of approximately 19-25 contiguous nucleotides (the "target sequence") in the target RNA. Generally, a target sequence on the target RNA can be selected from a given cDNA sequence corresponding to the target RNA, preferably beginning 50 to 100 nt downstream (i.e., in the 3' direction) from the start codon. The target sequence can, however, be located in the 5' or 3' untranslated regions, or in the region nearby the start codon. Techniques for selecting target sequences for siRNA's are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target RNA.

The siRNA of the invention can be obtained using a number of techniques known to those of skill in the art. For example, the siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharrnacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA of the invention to cells in vivo is discussed in more detail below.

siRNA of the invention can also be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol*, 20: 446-448; Brummelkamp T R et al. (2002), *Science* 296: 550-553; Miyagishi M et al. (2002), *Nat. Biotechnol*. 20: 497-500; Paddison P J et al. (2002), *Genes Dev*. 16: 948-958; Lee N S et al. (2002), *Nat. Biotechnol*. 20: 500-505; and Paul C P et al. (2002), *Nat. Biotechnol*. 20: 505-508, the entire disclosures of which are herein incorporated by reference.

The siRNA of the invention can also be expressed from recombinant viral vectors intracellularly in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap*. 2: 301-310; Eglitis M A (1988), *Biotechniques* 6: 608-614; Miller A D (1990), *Hum Gene Therap*. 1: 5-14; Anderson W F (1998), *Nature* 392: 25-30; and Rubinson D A et al., *Nat. Genet*. 33: 401-406, the entire disclosures of which are herein incorporated by reference.

Preferred viral vectors are those derived from AV and AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter. A suitable AV vector for expressing the siRNA of the invention, a method for constructing the recombinant AV vector, and a method for delivering the vector into target cells, are described in Xia H et al. (2002), *Nat. Biotech*. 20: 1006-1010. Suitable AAV vectors for expressing the siRNA of the invention, methods for constructing the recombinant AV vector, and methods for delivering the vectors into target cells are described in Samulski R et al. (1987), *J. Virol*. 61: 3096-3101; Fisher K J et al. (1996), *J. Virol*., 70: 520-532; Samulski R et al. (1989), *J. Virol*. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

pRb2/p130 expression can also be inhibited at the protein level by compounds such as anti-pRb2/p130 antibodies and anti-pRb2/p130 aptamers. Anti-pRb2/p130 antibodies can be generated from SEQ ID NO: 2 or immunogenic fragments thereof, by standard techniques. Antibodies can also be generated from pRb2/p130 protein isolated from a given subject (or expressed from a pRb2/p130 cDNA isolated from a given subject) to allow for "personalized treatment" of the subject's breast cancer. Anti-pRb2/p130 antibodies can be a monoclonal antibody, a polyclonal antibody or an antibody fragment that is capable of binding an epitope of SEQ ID NO: 2 or other pRb2/p130 protein. Such antibodies include chimeric, single chain, and humanized antibodies, as well as Fab fragments and the products of an Fab expression library.

Polyclonal anti-pRb2/p130 antibodies can be produced by immunizing an animal with substantially pure pRb2/p130 protein or an immunogenic fragment thereof, using techniques well-known in the art. Antibody fragments, such as Fab antibody fragments, which retain some ability to selectively bind to the antigen of the antibody from which they are derived, can be made using well known methods in the art. Such methods are generally described in U.S. Pat. No. 5,876,997, the entire disclosure of which is incorporated herein by reference.

Monoclonal anti-pRb2/p130 antibodies can be prepared using the method of Mishell, B. B. et al., *Selected Methods In Cellular Immunology*, (Freeman W H, ed.) San Francisco, 1980, the disclosure of which is herein incorporated by reference. Briefly, a peptide is used to immunize spleen cells of Balb/C mice. The immunized spleen cells are fused with myeloma cells. Fused cells containing spleen and myeloma cell characteristics are isolated by growth in HAT medium, a medium which kills both parental cells, but allows the fused products to survive and grow.

In another embodiment of the present invention, transcription of the ER-$\alpha$ gene can be activated by altering the methylation pattern of the ER-$\alpha$ gene promoter. For example, a DNA demethylating agent can be used to demethylate the ER-$\alpha$ gene promoter. As discussed above, this methylation pattern in the ER-$\alpha$ gene promoter results in an ER-$\alpha$ gene that is not transcriptionally repressed. By demethylating the ER-$\alpha$ gene promoter in this way, breast cancer cells which are initially ER-negative (and thus which have a higher metastatic potential and are refractory to anti-cancer drugs such as tamoxifen) can be converted into breast cancer cells which are ER-positive. As discussed above, breast cancer cells which are ER-positive have a lower metastatic potential and are more responsive to anti-cancer drugs (such as treatment with tamoxifen).

Suitable DNA demethylating agents include 5-azacytidine (5-aza) and 5-Aza-2'-deoxycytidine (5-Aza-2dc). In a preferred embodiment, the DNA-demethylating agent is 5-Aza-2dc. Methods for demethylating DNA and for determining the methylation pattern of the ER-$\alpha$ gene promoter are within the skill in the art, and representative techniques are given in the Examples below.

The invention also provides a method of treating estrogen receptor-negative breast cancer in a subject, by administering to that subject at least one compound that activates transcription of the ER-$\alpha$ gene, preferably by local administration to the tumor. Compounds which activate transcription of the ER-$\alpha$ gene are described above; for example, such compounds can inhibit expression of pRb2/p130 in the estrogen receptor-negative breast cells or can demethylate the ER-$\alpha$ gene promoter. Transcriptional activation of the ER-$\alpha$ gene by administering such compounds causes the estrogen receptor-negative breast cancer cells to become estrogen receptor-positive breast cancer cells. The subject can then undergo breast cancer therapy which targets estrogen receptor-positive breast cancer cells. For example, anti-estrogen therapeutics such as those described above can be administered to the subject using standard therapeutic regimens.

Thus in one embodiment of the invention, an effective amount of at least one compound which inhibits expression of pRb2/p130, or which demethylates the ER-$\alpha$ promoter, is administered to a subject suffering from estrogen receptor-negative breast cancer. Such compounds are described in detail above.

In the practice of the present method, an effective amount of at least one compound which activates transcription of the ER-$\alpha$ gene, such as those described above, is administered to a subject suffering from estrogen receptor-negative breast cancer. As used herein, an "effective amount of at least one compound which activates transcription of the ER-$\alpha$ gene" is an amount sufficient to remove the transcriptional repression of ER-$\alpha$ gene and restore ER-$\alpha$ gene expression to a cell. ER-$\alpha$ gene expression in a cell can be evaluated by methods within the skill in the art for determining levels of ER-$\alpha$ gene gene expression, or for determining the methylation pattern of the ER-$\alpha$ gene promoter.

For example, cell or tissue samples for use in determining levels of ER-$\alpha$ expression can be obtained by standard techniques, such as punch or needle biopsy, surgical biopsy, and the like. For example, a test sample of tissue or cells from a subject suspected of having breast cancer is obtained by surgical biopsy. As a control, a tissue or cell sample from unaffected breast tissues of the subject, or from a normal subject, is also obtained. The ER-$\alpha$ RNA or protein can then be isolated from the test and control samples using standard techniques, for determination of ER-$\alpha$ expression levels. Alternatively, the levels ER-$\alpha$ expression in a test sample can be compared to average levels of ER-$\alpha$ gene expression previously obtained for a population of normal control subjects.

Suitable techniques for determining the level of RNA transcripts of a particular gene in cells are within the skill in the art. According to one such method, total cellular RNA can be purified from cells by homogenization in the presence of nucleic acid extraction buffer, followed by centrifugation. Nucleic acids are then precipitated, and DNA is removed by treatment with DNase. The RNA molecules are then separated by gel electrophoresis on agarose gels according to standard techniques, and transferred to nitrocellulose or other suitable filters by, e.g., the so-called "Northern" blotting technique. The RNA is immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7, the entire disclosure of which is incorporated by reference.

Autoradiographic detection of probe hybridization to ER-$\alpha$ RNA can be performed by exposing hybridized filters to photographic film. Densitometric scanning of the photographic films exposed by the hybridized filters provides an accurate measurement of RNA transcript levels. Alternatively, RNA transcript levels can be quantified by computerized imaging of the hybridization filter, for example with the Molecular Dynamics 400-B 2D Phosphorimager available from Amersham Biosciences, Piscataway, N.J.

In addition to blotting hybridization techniques, detection of RNA transcripts from a given gene can be carried out by in situ hybridization. This technique requires fewer cells than the Northern blotting technique, and involves depositing whole cells onto a microscope cover slip and probing the nucleic acid content of the cell with a solution containing radioactive or otherwise labeled cDNA or cRNA probes. This technique is particularly well-suited for analyzing breast tissue biopsy samples. The practice of the in situ hybridization technique is described in more detail in U.S. Pat. No. 5,427,916, the entire disclosure of which is incorporated herein by reference.

The number of ER-α transcripts in test or control sample can also be determined by reverse transcription of ER-α transcripts, followed by amplification by polymerase chain reaction (RT-PCR). The levels of ER-α transcripts can be quantified in comparison with an internal standard; for example, by comparison to levels of mRNA produced from a "housekeeping" gene present in the same sample. A suitable "housekeeping" gene for use as an internal standard includes myosin, β-actin or glyceraldehyde-3-phosphate dehydrogenase (G3PDH). Methods of quantitative RT-PCR and variations thereon are within the skill in the art.

ER-α gene expression can also be determined by measuring the level of ER-α protein in a test sample versus a control sample. For example, test and control breast tissue samples can be obtained by surgical biopsy, as described above, and ER-α protein can be detected on the surface of the cells by standard immunodetection (e.g., immunofluorescent) techniques.

Other techniques for measuring pRb2/p130 protein levels are known in the art, and include electrophoretic separation and identification, peptide digestion, and sequence analysis; and immunoassays such as radioimmunoassays, ELISA (enzyme linked immunosorbent assay), "sandwich" immunoassays, gel diffusion precipitation reactions, in situ immunoassays, complement fixation assays, and immunoelectrophoretic assays. One skilled in the art can readily determine an effective amount of a compound which activates transcription of the ER-α gene to be administered to a given subject, by taking into account factors such as the size and weight of the subject; the extent of the breast tumor growth or disease penetration; the age, health and sex of the subject; the route of administration; and whether the administration is regional (e.g., local) or systemic.

Generally, an effective amount of a compound which activates transcription of the ER-α gene can comprise from about 5-3000 µg compound/kg of body weight, preferably between about 700-1000 µg compound/kg of body weight, and more preferably greater than about 1000 µg compound/kg of body weight. If the compound which activates transcription of the ER-α gene is a compound that inhibits expression of pRb2/p130, and that compound comprises a nucleic acid, an effective amount of such a compound can comprise an intercellular concentration at or near the tumor site of from about 1 nanomolar (nM) to about 100 nM, preferably from about 2 nM to about 50 mM, more preferably from about 2.5 nM to about 10 nM. It is contemplated that greater or lesser amounts of the compounds of the invention can be administered to a subject.

Compounds which activate transcription of the ER-α gene can be administered to a subject by any means suitable for exposing breast cancer cells to the compound. For example, the compound can be administered by gene gun, electroporation, or by other suitable parenteral or enteral administration routes. Suitable enteral administration routes include oral, rectal, or intranasal delivery. Suitable parenteral administration routes include intravascular administration (e.g., intravenous bolus injection, intravenous infusion, intra-arterial bolus injection, intra-arterial infusion and catheter instillation into the vasculature); peri-tumoral and intra-tumoral injection; subcutaneous injection or deposition including subcutaneous infusion (such as by osmotic pumps); direct application to the tissue of interest, for example by a catheter or other placement device (e.g., a suppository or an implant comprising a porous, non-porous, or gelatinous material); and inhalation. Preferably, a compound which inhibits pRb2/p130 expression is administered by injection or infusion, more preferably by direct injection into a tumor.

One skilled in the art can also readily determine an appropriate dosage regimen for administering compounds which activate transcription of the ER-α gene t o a subject. For example, the compound can be administered to the subject once, for example as a single injection or deposition. Alternatively, the compound can be administered once or twice daily to a subject for a period of from about three to about twenty-eight days, more preferably from about seven to about ten days. In a preferred dosage regimen, the compound is injected once a day for seven days. Where a dosage regimen comprises multiple administrations, it is understood that the effective amount of compound administered to the subject can comprise the total amount of the compound administered over the entire dosage regimen.

Those compounds which activates transcription of the ER-α gene (in particular those which comprise nucleic acids, such as the antisense oligonucleotides or siRNA described above), can also be administered to the subject either as naked compound, or can be administered in conjunction with a delivery reagent. Suitable delivery reagents include the Mirus Transit TKO lipophilic reagent; lipofectin; lipofectamine; cellfectin; or polycations (e.g., polylysine), and liposomes.

A preferred delivery reagent for compounds which activates transcription of the ER-α gene is a liposome. For example, liposomes can aid in the delivery of a nucleic acid or nucleotide to a particular tissue, such as tumor tissue, and can also increase the blood half-life of the nucleic acid or nucleotide. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., 1980, *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Liposomes encapsulating the compounds which activate transcription of the ER-α gene preferably comprise a ligand molecule that can target the liposome to breast tumor cells. Particularly preferably, the liposomes encapsulating these compounds are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptalce of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), *P.N.A.S., USA*, 18: 6949-53. In addition, the reduced uptake by the RES lowers the toxicity of stealth liposomes by preventing significant accumulation in the liver and spleen. Thus, liposomes of the invention that are modified with opsonization-inhibition moieties are particularly suited to deliver compounds which inhibit pRb2/p130 expression which comprise nucleic acids to breast tumor cells.

Opsonization inhibiting moieties suitable for modifying liposomes are preferably water-soluble polymers with a number average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPQ, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

It is understood that the present methods can be used to maintain the expression of the ER-α gene in ER-positive breast cancer cells. Thus, ER-positive breast cancer cells can also be subjected inhibition of pRb2/p130 expression or demethylation of the ER-α gene promoter as described above. ER-positive breast cancer cells treated in this way will not spontaneously convert into ER-negative breast cancer cells, because the ER-α gene will remain transcriptionally active. Thus, the invention provides a method of maintaining ER-α gene expression in ER-positive breast cancer cells, so that such cells maintain a low metastatic potential, and remain sensitive to anti-cancer drugs such as tamoxifen.

The compounds of the invention which activate transcription of the ER-α gene can be formulated as pharmaceutical compositions or medicaments prior to administering to a subject, according to techniques known in the art. Thus, the use of a compound which i activate transcription of the ER-α gene in estrogen receptor-negative breast cancer cells, for the production of a pharmaceutical composition or medicament for the treatment of estrogen receptor-negative breast cancer, is specifically contemplated by the present invention.

Pharmaceutical compositions or medicaments of the present invention are characterized as being at least sterile and pyrogen-free. As used herein, "pharmaceutical formulations" or "medicaments" include formulations for human and veterinary use. Methods for preparing pharmaceutical compositions and medicaments of the invention are within the skill in the art, for example as described in *Remington's Pharmaceutical Science*, 17th ed., Mack Publishing Company, Easton, Pa. (1985), the entire disclosure of which is herein incorporated by reference.

The present pharmaceutical formulations or medicaments comprise at least one compound which activate transcription of the ER-α gene (e.g., 0.1 to 90% by weight), or a physiologically acceptable salt thereof, mixed with a physiologically acceptable carrier. Preferred physiologically acceptable carriers are water, buffered water, normal saline, 0.4% saline, 0.3% glycine, hyaluronic acid and the like.

Pharmaceutical compositions or medicaments of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, preferably 25%-75%, of one or more compounds of the invention which activate transcription of the ER-α gene. A pharmaceutical composition or medicament for aerosol (inhalational) administration can comprise 0.01-20% by weight, preferably 1%-10% by weight, of compounds of the invention which activate transcription of the ER-α gene that are encapsulated in a liposome as described above, and propellant. A carrier can also be included as desired; e.g., lecithin for intranasal delivery.

The invention will now be illustrated by the following non-limiting examples.

EXAMPLES

The following materials and methods used in the Examples described below.

Cell Lines and Primary Tumors

The breast carcinoma cell lines, MCF-7 (estrogen receptor-positive), MDA-MB-231 (estrogen receptor-negative) and the normal mammary epithelial cell line MCF-12A, were obtained from ATCC (Rockville, Md.) and were cultured according to the manufacturer's protocols. The breast primary tumors were selected on the basis of estrogen receptor status.

Methylation Specific-PCR (MSP)

Genomic DNA from cell lines and primary tumors were subjected to modification by sodium bisulfite in order to convert unmethylated cytosines but not methylated cytosines to uracils (GpGenome DNA modification kit, Intergene Company). DNA modified by bisulfite reaction was used to amplify regions within ER-α and ERβ promoters containing CpG islands by PCR. Ten pairs of ER-α primers (Lapidus et al, 1998) and four pairs of ER-β primers (region a:

```
betaM1 forward
5'-AAATTTGTTAGTTGGATTAGATCGA-3';        (SEQ ID NO:3)

betaM2 reverse
5'-TTCAAAAAAACCTTTAATTAAAACG-3';        (SEQ ID NO:4)

betaU1 forward
5'-AAATTTGTTAGTTGGATTAGATTGA-3';        (SEQ ID NO:5)

betaU2 reverse
5'-CAAAAAAACCTTTAATTAAAACACA-3';        (SEQ ID NO:6)

region b: betaM3 reverse
5'-AAACGACGAACGCTAAACCGAAAAAAAA-3';     (SEQ ID NO:7)

betaU3 reverse
5'-AACAAACAACAAACACTAAACCAAAAAAAAA-3'  (SEQ ID NO:8)
``` were designed to discriminate between modified (M) and unmodified (U) DNA. As a control, the following wild-type primers were used to amplify the DNA not subjected to sodium bisulfite modification:

```
WTalfa1 forward
5'-AGGAGCTGGCGGAGGGCGTTCG-3';           (SEQ ID NO:9)

WTalfa2 reverse
5'-AGCGCATGTCCCGCCGACACGC-3';           (SEQ ID NO:10)

WTbeta1 forward
5'-CGAGCGCTGGGCCGGGGAGGG-3';            (SEQ ID NO:11)

WTbeta2 reverse
5'-CTCCCGGCGCGCGCCCCGCC-3'.             (SEQ ID NO:12)
```

Cross-Linked Chromatin Immunoprecipitation (XChIP) to Determine In Vivo ER-α and ER-β Promoter Occupancy Chromatin immunoprecipitations were performed using a modified procedure of previously published methods (see Orlando et al., 1997, Methods and 11, 205; Keller et al., 2002, J. Biol. Chem., 277, 31430, the entire disclosures of which are herein incorporated by reference), in combination with Western blot and PCR techniques. Approximately 1×10$^6$ MCF-7 and MDA-MB-231 cells were cross-linked by adding formaldehyde (1% final concentration) directly to the culture medium, and incubating the cells for 8 minutes at 37° C.

After removal of the medium, cells were washed three times on plates with cold phosphate-buffered saline (PBS) containing protease inhibitors (1 mM phenylmethyl-sulfonyl fluoride, 1 μg/ml aprotinin and 1 μg/ml pepstatin A), scraped, and washed again twice in cold PBS. The cell pellet was resuspended in SDS lysis buffer (1% SDS, 10 mM EDTA, 50 mM Tris-HCl, pH 8.1), incubated for 10 minutes on ice, sonicated to shear DNA to lengths between 300 and 500 bp, and centrifuged for 10 minutes at 13,000 rpm at 4° C. Sonicated cell supernatant was diluted in ChIP dilution buffer (0.01% SDS, 1.1% Triton X-100, 1.2 mM EDTA, 16.7 mM Tris-HCL, pH 8.1, 167 mM NaCL), and pre-cleared twice with salmon sperm DNA/protein A agarose at 4° C. for 2 hours. The agarose was pelleted and the supernatant fraction was collected and incubated overnight at 4° C. with the immunoprecipitating antibody.

Each immunoprecipitation was performed using 3-4 μg of antibodies against pRb2/p130, E2F4, E2F5, HDAC1, SUV39H1, p300, DNMT1, acetylated histones H3 and H4 (Santa Cruz Biotechnology, CA and Upstate Biotechnology, MA). As negative controls, a "no-antibody" immunoprecipitation was performed by incubating the supernatant fraction with salmon sperm DNA/protein A agarose, and immunoprecipitating the mixture with an irrelevant antibody. The immunocomplexes-DNA were recovered with 50 μl of salmon sperm DNA/protein A agarose, and washed two times with Low Salt Wash Buffer (1% Triton X-100, 0.1% SDS, 2 mM EDTA, 20 mM Tris-HCl, pH 8.1, 150 mM NaCL), with High Salt Wash Buffer (1% Triton X-100, 0.1% SDS, 2 mM EDTA, 20 mM Tris-HCl, pH 8.1, 500 mM NaCL), with Lithium Wash Buffer (0.25M LiCL, 1% NP40, 1% deoxycholate, 1 mM EDTA, 10 mM Tris-HCl, pH 8.1) and four times with 1×TE Buffer (10 mM Tris-HCL, 1 mM EDTA, pH 8.0).

The washed immunocomplexes-DNA/protein A were divided for Western blotting and DNA extraction. For Western blot analysis, the samples were eluted from the beads, loaded in an SDS-polyacrylamide gel and transferred to a blotting membrane. The immunoblotting was performed using antibodies against pRb2/p130, E2F4, E2F5, HDAC1, SUV39H1 DNMT1, and p300 (Santa Cruz Biotechnology, CA and Upstate Biotechnology, MA).

For DNA extraction, Elution Buffer (1% SDS, 0.1M NaHCO$_3$) was added to the washed immunocomplexes-DNA/protein A. Cross-links were reversed by incubating the samples) at 65° C. overnight, and DNA was extracted with phenol:chloroform and ethanol precipitation. DNA pellets were resuspended in Tris-EDTA buffer (TE), and PCR was performed using specific primers to amplify the ER-α promoter (forward 5'AGGAGCTGGCGGAGGG CGTTCG-3' (SEQ ID NO:13); reverse 5'-AGCGCATGTCCCGCCGA-CACGC-3') (SEQ ID NO:14) and ER-β promoter (forward 5'-CGAGCGCTGGGCCGGGGAGGG-3' (SEQ ID NO:15); reverse 5'-CTCCCGGCGCGCGCCCCGCC-3' (SEQ ID NO:16)). The total chromatin (input) was used as a positive control in the PCR reactions.

Example 1

Figure 1A:
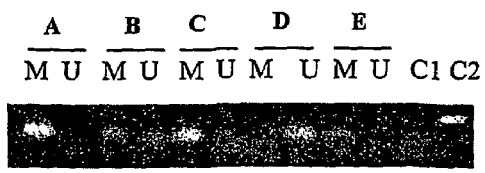
Figure 1B:
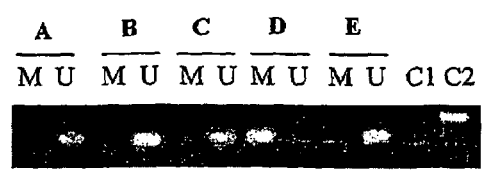
Figure 1C:
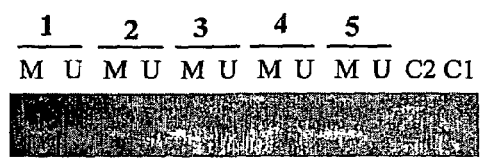
Figure 1D:
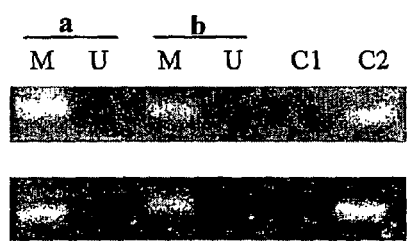

The Density of Methylated Sites of the ER-α and ER-β Promoters Influenced the Expression of These Genes The DNA methylation levels of estrogen receptor ER-α promoter in cycling MDA-MB-231 (estrogen-negative), MCF-7 (estrogen-positive), and MCF-12A (normal epithelial mammary) cell lines were investigated. Five regions of the ER-α promoter were analyzed by Methylation Specific-PCR (MSP) and a different density of CpG dinucleotides methylated in the MDA-MB-231 and MCF-7 breast cancer cell lines was found. In the MDA-MB-231 cells, the regions A, B, C, E on the ER-α promoter were found to be methylated, and region D was unmethylated (FIG. 1a). On the contrary, in the MCF-7 cell line, only the D region was methylated (FIG. 1b). In MCF-12A cells, all the analyzed regions of the ER-α promoter were unmethylated. Moreover, region D of the ER-α promoter in primary breast tumors was methylated in five samples (FIG. 1c). Interestingly, these primary tumors were classified as ER-α positive at the time of diagnosis via immunohistochemistry. Finally, the methylation level of two ER-β promoter regions wee both methylated in MCF-7 and MDA-MB-231 cells (FIG. 1d).

These data indicate that a high density of CpG sites methylated in the ER-α promoter are responsible for transcriptional de-activation of the ER-α gene in ER-negative MDA-MB-231 cells. Moreover, the presence of ER-β methylation in both MDA-MB-231 and MCF-7 cell, lines could explain the lack of ER-β expression in these cell lines.

Example 2

In Vivo ER Promoter Occupancy by pRb2/p130

Figure 2A:
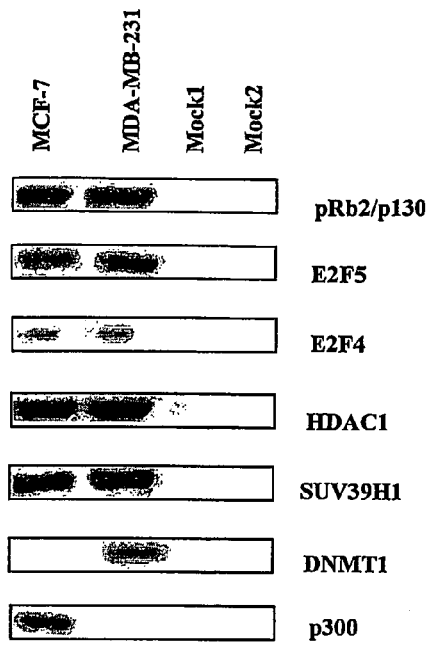
FIGS. 2a-2d show formaldehyde cross-linked chromatin immunoprecipitation (XChIP) analyses in vivo ER-α promoter occupancy by pRb2/p130-E2F4/5-HDAC1-SUV39H1-DNMT1-p300 in cycling MCF-7 and MDA-MB-231 breast cancer cell lines.
Figure 2B:
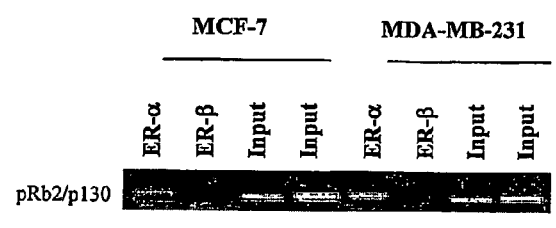
Figure 2C:
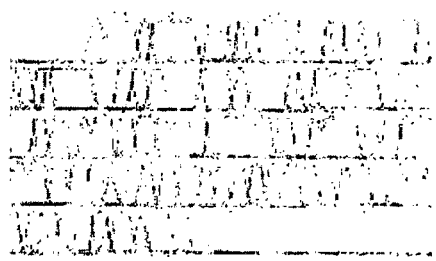
Figure 2D:

A modified procedure of formaldehyde cross-linked chromatin immunoprecipitation assay (XChIP) was used, in combination with Western blotting and PCR, to study in vivo ER-α and ER-β promoter occupancy by pRb2/p130. It was found that complexes formed by pRb2/p130-E2F4/5-HDAC1-SUV39H1-p300 and pRb2/p130-E2F4/5-HDAC1-SUV39H1-DNMT1 bound the ER-α promoter—but not ER-β promoter—in cycling MCF-7 and MDA-MB-231 breast cancer cell lines, respectively (See FIGS. 2a, b, c and d). Interestingly, the ER-α promoter region, bound by the aforementioned complexes, contains two E2F sites near the transcription start that could be potential sites of binding for the pRb2/p130 multimolecular complexes. In addition, TATA and CAAT boxes are located downstream from the E2F sites. These data and observations indicate that the presence of pRb2/p130-E2F4/5-HDAC1-SUV39H1-p300 and pRb2/p3130-E2F4/5-HDAC1-SUV39H1-DNMT1 complexes could regulate ER-α gene transcription, perhaps by modulating chromatin packaging and the accessibility of the ER-α gene to the basal transcription machinery. It is possible that pRb2/p130 could mediate transcriptional repression by first bringing a specific histone methyltansferase (SUV39H1) and deacetylase (HDAC1) onto the ER-α promoter for transient silencing of this gene. In a second repression step, pRb2/p130 could further recruit the DNMT1 to methylate ER-α promoter DNA for long-term gene silencing.

Indeed, in the ER-α-positive MCF-7 cell line, there was only one methylated CpG region among those that were screened, and that the complex found by XChIP seems to be depleted of DNMT1. On the other hand, the ER-α-negative MDA-MB-231 cell line showed methylation in the majority of the CpG regions screened, and the complex contained DNMT1. Without wishing to be bound by any theory, the shift from ER-α activation to ER-α silencing could therefore depend on balance among histone deacetylation/acetylation, histone methylation and DNA methylation, possibly regulated by replacement of histone acetyl transferase p300 with DNMT1 in pRb2/p130-E2F4/5-HDAC1-SUV39H1 complexes.

Collectively, these results provide the physiological evidence for a link between pRb2/p130 and chromatin-modifying enzymes in ER-α, but not ER-β, transcriptional regulation in breast cancer cell lines.

Example 3

Figure 3:
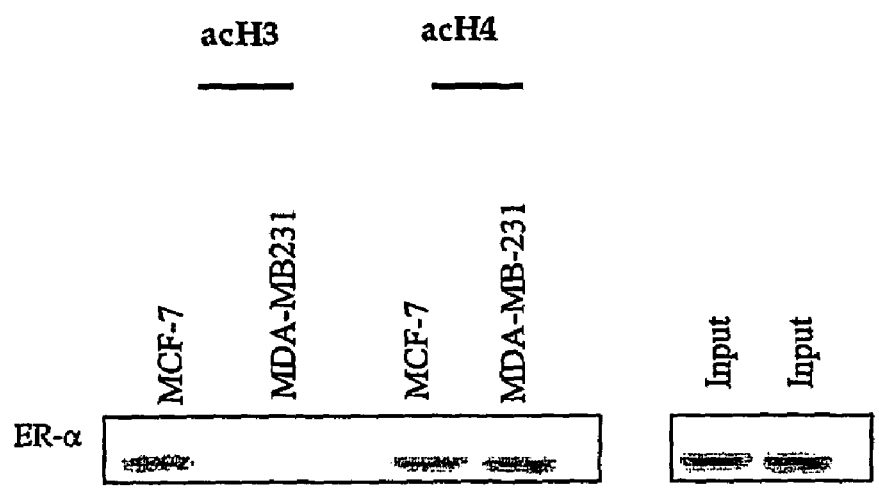
FIG. 3 shows formaldehyde cross-linked chromatin immunoprecipitations (XChIPs) histone acetylation levels of ER-α promoter in MDA-MB231 and MCF-7 breast cancer cell lines. The input represents the total chromatin prior to immunoprecipitation.

Histone Acetylation Levels of ER-α Promoter Correlate with ER-α Gene Transcriptional Activation Having identified the pRb2/p130 multimolecular complexes on the ER-α promoter, the relative levels of ER-α histone H3 and H4 acetylation in MDA-MB-231 and MCF-7 cell lines were then determined. A correlation between acetylation of histone H3 and H4 and the activation of ER-α gene was found. Interestingly, levels of acetylated histone H4 and H3 were detected in MCF-7 cells, whereas only histone H4 acetylation was detected in the MDA-MB-231 cell line (FIG. 3). The interplay among pRb2/p130, HDAC1, p300, SUV39H1 and DNMT1, is not clear from these data, but the presence of different enzymes in the complexes with pRb2/p130 suggest that these complexes could mediate HAT activity, with distinct effects. In other words, and without wishing to be bound by any theory, the presence of DNMT1 in complexes with pRb2/p130, HDAC1 and SUV39H1 might function in the maintenance of an ER-α transcriptional-repressive state, by occluding p300 association in MDA-MB-231 cells and leading to higher order chromatin structure that denies access of the gene to transcription factors. On the other hand, the absence of DNMT1 in the pRb2/p130 multimolecular complex could facilitate the p300 recruitment required to maintain high levels of histone acetylation on the ER-α promoter, thus leading to its transcriptional activation of the gene in MCF-7 cells.

Furthermore, the absence of histone H3 acetylation in MDA-MB-231 cells was correlated with gene silencing. In fact, it has been reported that methylation and acetylation of histone H3 are mutually exclusive, and that H3 acetylation correlates with transcriptional activation. This is consistent with the present finding that, in MDA-MB-231 cells, SUV39H1 methylated histone H3 while (in MCF-7 cells) histone methyltransferase activity was prevented by p300 activity, which can acetylate histone H3.

Example 4

Effects of a Demethylating Agent 5-Aza-2dC on the Expression of ER-α in MDA-MB-231 Cells MDA-MB-231 cells were grown in DMEM medium to a density of $5\times10^5$ cells/100-mm plate, and were treated with 2.5 µM of the DNA methyltransferase inhibitor 5-Aza-2-deoxicytidine (5-Aza-2dC) for 24, 36, 48, 72, and 96 hours. Control cells were left untreated. Total RNA was isolated from the treated and control cells, and ER-α RNA was detected by reverse-transcription polymerase chain reaction (RT-PCR). P-actin RNA expression was also determined by RT-PCR in total RNA isolated from treatment and control cells to normalize RNA loading. ER-α protein was detected by Western blot using whole cell lysates obtained from MDA-MB-231 cells untreated or treated with 2.5 µM 5-Aza-2dC for 24, 36, 48, 72, and 96 hours. The expression of β-actin protein was assessed to normalize protein loading.

Figure 5A:
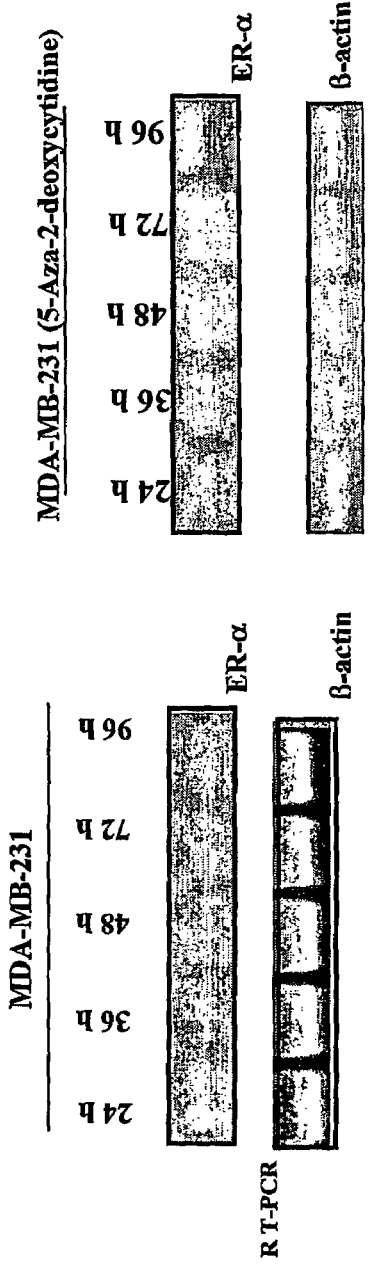
FIGS. 5a-5b show the effects of 5-Aza-2dC on ER-α RNA and protein expression in MDA-MB-231 cells.
Figure 5B:
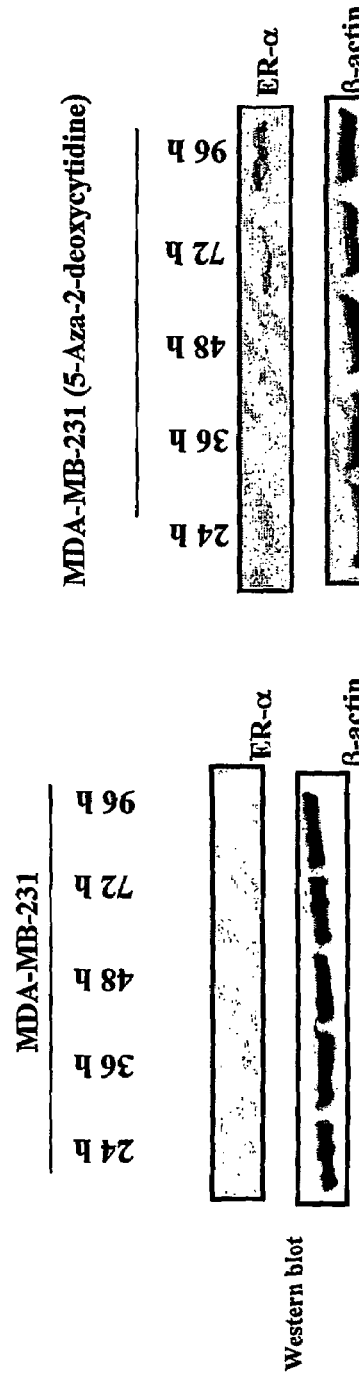

Treatment of MCF-7 cells with 5-Aza-2dC did not significantly influence the expression of ER-α RNA or protein in the cells. However, as can be seen from FIGS. 5a and 5b, respectively, the treatment significantly enhanced the expression of ER-α RNA and protein in MDA-MB-231 cells, which was especially evident at longer time-points (e.g., 48-96 h).

Example 5

ER-α Promoter Occupancy by pRb2/p130-Multimolecular Complex in 5-Aza-2dC Treated MDA-MB-231 and MCF-7 Cells The recruitment of pRb2/p130-multimolecular complexes to ER-α promoter was analyzed in MCF-7 and MDA-MB-231 cells by XChIP. The cells were treated with 5-Aza-2dC for 72 hours, and cross-linked with formaldehyde. Soluble chromatin was immunoprecipitated with specific antibodies recognizing pRb2/p130, E2F4, HDAC1, SUV39H1, DNMT1, and p300. The presence of ER-α promoter sequences in the immunoprecipitates was tested by PCR using the specific primers spanning ER-α promoter set forth above.

Figure 6:
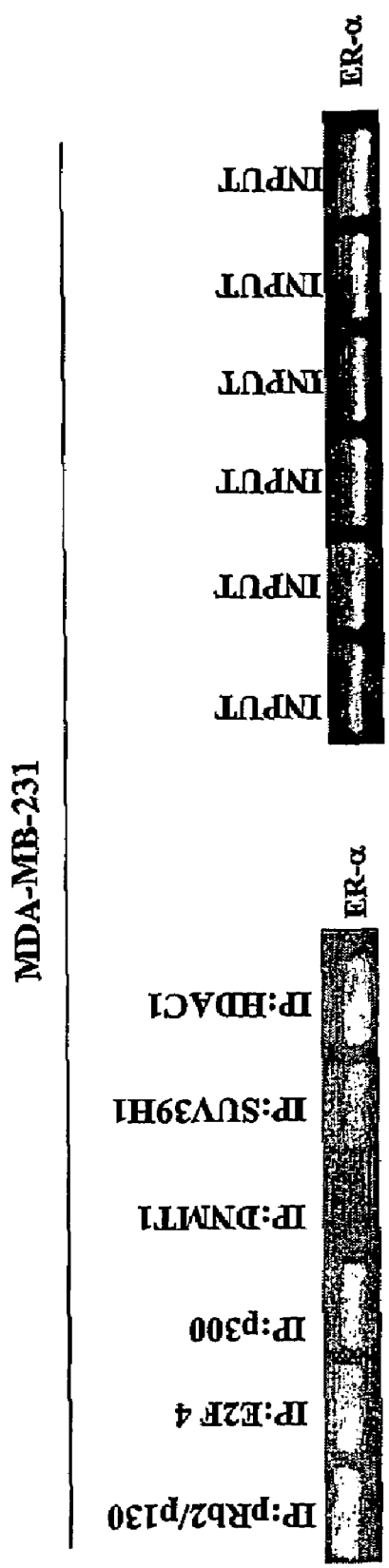
FIG. 6 shows XChIP analyses of the recruitment of pRb2/p130-multimolecular complexes to ER-α promoter in MDA-MB-231 cells. The cells were treated with 5-Aza-2dC for 72 hours and cross-linked with formaldehyde. Soluble chromatin was immunoprecipitated with specific antibodies recognizing pRb2/p130, E2F4, HDAC1, SUV39H1, DNMT1, and p300. The presence of ER-α promoter sequences in the immunoprecipitates was tested by PCR using specific primers spanning ER-α promoter.
Figure 7B:
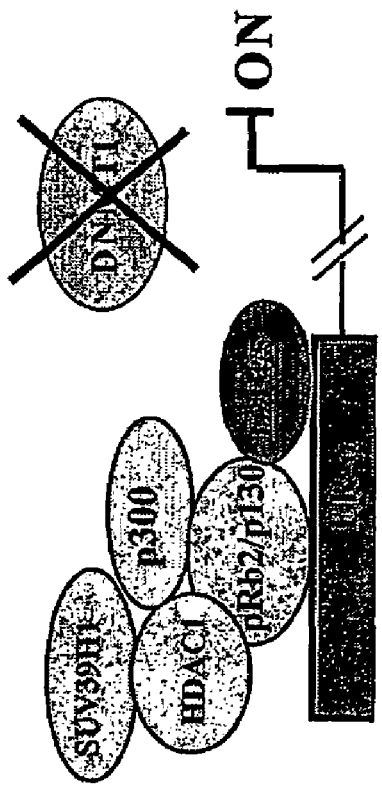
FIGS. 7a-7b illustrate a proposed model of 5-Aza-2dC action on ER-α promoter in MDA-MB-231 cells.
Figure 7A:
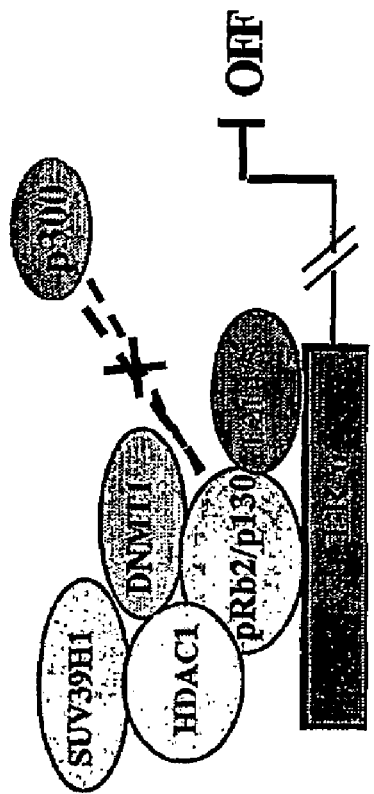

As can be seen from FIG. 6, at the time of maximal ER-α RNA expression (72 h MDA) in 5-Aza-2dC treated MDA-MB-231 cells, a specific pRb2/p130-multimolecular complex was recruited to the ER-α promoter. This complex contained pRb2/p130, E2F4, SUV39H1, p300, and HDAC1, but did not contain DNMT1. This complex is therefore identical to the complex that was previously demonstrated to be associated with the ER-α promoter in untreated MCF-7 cells. In contrast, 5-Aza-2dC treatment of in MCF-7 cells did not influence the composition of the pRb2/p130-multimolecular complex that was recruited onto the ER-α promoter in that cell line, since this complex was identical to the complex that was previously demonstrated to be bound to the ER-α promoter in untreated MCF-7 cells. The proposed model of the effect of 5-Aza-2dc action on binding of chromatin-modifying enzymes to the ER-α promoter is shown in FIG. 7.

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

I claim:

1. A method of diagnosing breast cancer, comprising the steps of:
   (1) obtaining a sample of breast cancer cells; and
   (2) determining the DNA methylation pattern of the ER-α gene promoter in the cells, wherein:
      (i) the presence of DNA methylation in the A, B, C and E regions of the ER-α gene promoter in the cells indicates that the cells are estrogen receptor-negative; and
      (ii) no DNA methylation in the ER-α gene promoter of the cells, or the presence of DNA methylation only in the D region of the ER-α gene promoter in the cells, indicates that the cells are estrogen receptor-positive
      (iii) step 2 further comprising detecting a multimolecular complex bound to the ER-α gene promoter, and wherein:
         (a) the presence of DNA methylation in the A, B, C and E regions of the ER-α gene promoter in the cells, and the presence of pRb2/p130-E2F4/5-HDAC1-DNMT1-SUV39H1 complex bound to the ER-α gene promoter in the cells, indicates that the cells are estrogen receptor-negative; and
         (b) no DNA methylation in the ER-α gene promoter of the cells or the presence of DNA methylation only in the D region of the ER-α gene promoter in the cells, and the presence of pRb2/p130-E2F4/5-HDAC1-SUV39H1-P300 complex bound to the ER-α gene promoter in the cells, indicates that the cells are estrogen receptor-positive.

2. A method of determining the prognosis of a subject suffering from breast cancer, comprising the steps of:
   (1) obtaining a sample of breast cancer cells from a subject suffering from breast cancer; and
   (2) determining the DNA methylation pattern of the ER-α gene promoter in the test cells, wherein:
      (i) the presence of DNA methylation in the A, B, C and E regions of the ER-α gene promoter indicates that the subject has estrogen receptor-negative breast cancer and that the subject has a poor prognosis; or
      (ii) no DNA methylation in the ER-α gene promoter, or the presence of DNA methylation only in the D region of the ER-α gene promoter, indicates that the subject has estrogen receptor-positive breast cancer and that the subject has a favorable prognosis
      (iii) step 2 further comprising detecting a multimolecular complex bound to the ER-α gene promoter, and wherein:
         (a) the presence of DNA methylation in the A, B, C and E regions of the ER-α gene promoter in the cells, and the presence of pRb2/p130-E2F4/5-HDAC1-DNMT1-SUV39H1 complex bound to the ER-α gene promoter in the cells, indicates that the subject has estrogen receptor-negative breast cancer and that the subject has a poor prognosis; and
         (b) no DNA methylation in the ER-α gene promoter of the cells or the presence of DNA methylation only in the D region of the ER-α gene promoter in the cells, and the presence of pRb2/p130-E2F4/5-HDAC1-SUV39H1-p300 complex bound to the ER-α gene promoter in the cells, indicates that the subject has estrogen receptor-positive breast cancer and that the subject has a favorable prognosis.

3. The method of claim 2, wherein the test cells are obtained by surgical biopsy.

4. The method of claim 1, wherein the test cells are obtained by surgical biopsy.

* * * * *